US012718928B2

(12) United States Patent
Janiczek

(10) Patent No.: US 12,718,928 B2
(45) Date of Patent: Aug. 25, 2026

(54) SYSTEMS AND METHODS FOR TRACKING NEUROLOGICAL IMPROVEMENTS

(71) Applicant: Flourish Worldwide, LLC, Denver, CO (US)

(72) Inventor: Joseph J. Janiczek, Englewood, CO (US)

(73) Assignee: Flourish Worldwide, LLC, Denver, CO (US)

( * ) Notice: Subject to any disclaimer, the term of this patent is extended or adjusted under 35 U.S.C. 154(b) by 2 days.

(21) Appl. No.: 18/778,066

(22) Filed: Jul. 19, 2024

(65) Prior Publication Data

US 2026/0024647 A1 Jan. 22, 2026

(51) Int. Cl.

| | |
|---|---|
| ***G16H 20/70*** | (2018.01) |
| ***G06N 3/092*** | (2023.01) |
| ***G16H 20/30*** | (2018.01) |

(52) U.S. Cl.
CPC ............. *G16H 20/70* (2018.01); *G06N 3/092* (2023.01); *G16H 20/30* (2018.01)

(58) Field of Classification Search
CPC ........ G16H 20/70; G16H 20/00; G16H 20/30; G06N 3/092
USPC .............................................................. 705/2
See application file for complete search history.

(56) References Cited

U.S. PATENT DOCUMENTS

| | | | | |
|---|---|---|---|---|
| 10,453,356 | B2 | 10/2019 | Petrov | |
| 2016/0321946 | A1 | 11/2016 | Kim | |
| 2017/0287354 | A1 | 10/2017 | Miller | |
| 2020/0261019 | A1 * | 8/2020 | Sherpa | A61B 5/02055 |
| 2022/0122716 | A1 | 4/2022 | Sadow | |
| 2022/0187847 | A1 * | 6/2022 | Cella | G06Q 10/0833 |
| 2024/0029886 | A1 * | 1/2024 | Abel Fernandez | A61B 5/162 |
| 2024/0149066 | A1 * | 5/2024 | Bokil | A61N 1/36175 |
| 2025/0335509 | A1 * | 10/2025 | Nascimento | G06F 16/90332 |
| 2026/0018306 | A1 * | 1/2026 | Awasthi | G16H 10/60 |

FOREIGN PATENT DOCUMENTS

| | | | |
|---|---|---|---|
| WO | 2023172056 | A1 | 9/2023 |

* cited by examiner

*Primary Examiner* — Igor N Borissov
(74) *Attorney, Agent, or Firm* — Caldwell LLC

(57) ABSTRACT

A system for tracking neurological improvements, the system including a processor and a memory communicatively connected to the processor, the memory containing instructions configuring the processor to receive user data pertaining to a user, wherein the user data is associated with at least a neurological behavior, generate a habituation program as a function of the user data and a machine learning process, wherein generating the habituation program includes iteratively training a habituation machine learning model by receiving feedback data and adjusting one or more parameter values of the habituation machine learning model as a function of the feedback data, track a user's adaptability to the habituation program and generate an updated habituation program as a function of the user's adaptability to habituation program.

20 Claims, 14 Drawing Sheets

200

| | | |
|---|---|---|
| Vocational 204 | Marriage 208 | Family 212 |
| Health 216 | Virtue 220 | Emotional 224 |
| Financial 228 | Spiritual 232 | Intellectual 236 |
| Lifestyle 240 | Interest 244 | Social 248 |

FIG. 2

SYSTEMS AND METHODS FOR TRACKING NEUROLOGICAL IMPROVEMENTS

FIELD OF THE INVENTION

The present invention generally relates to the field of machine learning models. In particular, the present invention is directed to systems and methods for tracking neurological improvements.

BACKGROUND

Current systems utilized to track neurological conditions and provide treatment, fail to iteratively refine treatments or outputs based on the progress of the user. Instead, Outputs of current systems may be generic and lack adaptability.

SUMMARY OF THE DISCLOSURE

In an aspect a system for tracking neurological improvements is described. The system includes a processor and a memory communicatively connected to the processor, The memory contains instructions configuring the processor to receive user data pertaining to a user, wherein the user data is associated with at least a neurological behavior, generate a habituation program as a function of the user data and a machine learning process, wherein generating the habituation program includes iteratively training a habituation machine learning model by receiving feedback data and adjusting one or more parameter values of the habituation machine learning model as a function of the feedback data, track a user's adaptability to the habituation program and generate an updated habituation program as a function of the user's adaptability to habituation program.

In another aspect a method for tracking neurological improvements is described. The method includes the steps of receiving, by at least a processor, user data pertaining to a user, wherein the user data is associated with at least a neurological behavior, generating, by the at least a processor, a habituation program as a function of the user data and a machine learning process, wherein generating the habituation program includes iteratively training a habituation machine learning model by receiving feedback data and adjusting one or more parameter values of the habituation machine learning model as a function of the feedback data, tracking, by the at least a processor, a user's adaptability to the habituation program and generating, by the at least a processor, an updated habituation program as a function of the user's adaptability to the habituation program.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein:

FIG. 2 is a table illustrating exemplary domains;

DETAILED DESCRIPTION

At a high level, aspects of the present disclosure are directed to systems and methods for tracking neurological improvements. In an embodiments, the present disclosure discusses receiving user data, generating a habituation program, determining the user's adaptability to the habituation program, and updating the habituation program. In an embodiments, the present disclosure describes the use of machine learning models wherein parameter values of the machine learning models are iteratively changed in order to train the machine learning models.

Aspects of the present disclosure can be used to generate treatments for neurological behaviors and update treatments based on the user's adherence to the treatments. Exemplary embodiments illustrating aspects of the present disclosure are described below in the context of several specific examples.

Figure 1:
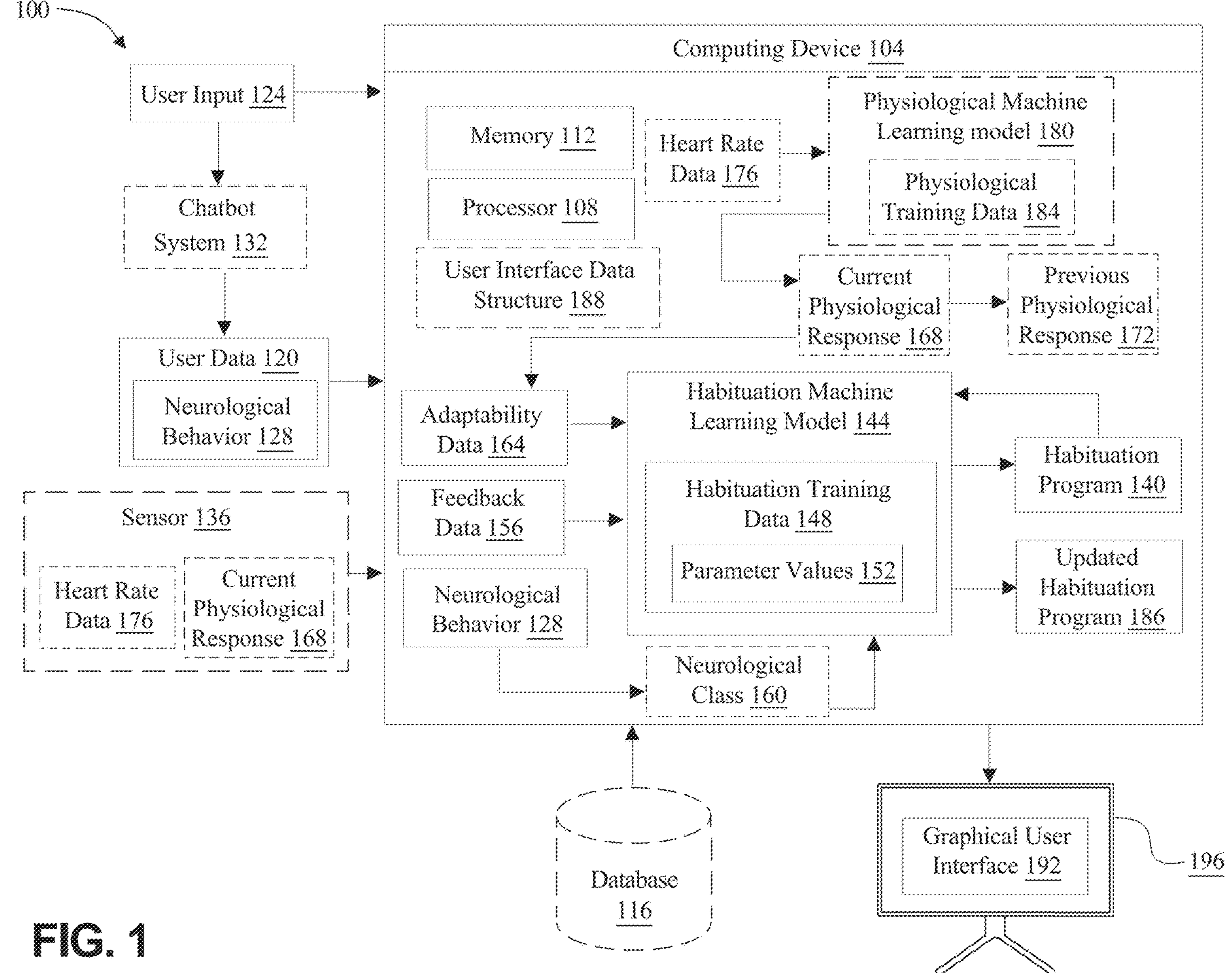
FIG. 1 is an exemplary embodiment of a system for tracking neurological improvements in accordance with the subject disclosure.

Referring now to FIG. 1, a system 100 for training machine learning models using unlabeled electrocardiogram data is described. System 100 includes a computing device 104. System 100 includes a processor 108. Processor 108 may include, without limitation, any processor 108 described in this disclosure. Processor 108 may be included in a and/or consistent with computing device 104. In one or more embodiments, processor 108 may include a multi-core processor. In one or more embodiments, multi-core processor may include multiple processor cores and/or individual processing units. "Processing unit" for the purposes of this disclosure is a device that is capable of executing instructions and performing calculations for a computing device 104. In one or more embodiments, processing units may retrieve instructions from a memory, decode the data, secure functions and transmit the functions back to the memory. In one or more embodiments, processing units may include an arithmetic logic unit (ALU) wherein the ALU is responsible for carrying out arithmetic and logical operations. This may include, addition, subtraction, multiplication, comparing two data, contrasting two data and the like. In one or more embodiments, processing unit may include a control unit wherein the control unit manages execution of instructions such that they are performed in the correct order. In none or more embodiments, processing unit may include registers wherein the registers may be used for temporary storage of data such as inputs fed into the processor and/or outputs executed by the processor. In one or more embodiments, processing unit may include cache memory wherein memory may be retrieved from cache memory for retrieval of data. In one or more embodiments, processing unit may include a clock register wherein the clock register is configured to synchronize the processor with other computing components. In one or more embodiments, processor 108 may include more than one processing unit having at least one or more arithmetic and logic units (ALUs) with hardware components that may perform arithmetic and logic operations. Processing units may further include registers to hold operands and results, as well as potentially "reservation station" queues of registers, registers to store interim results in multi-cycle operations, and an instruction unit/control circuit (including e.g. a finite state machine and/or multiplexor) that reads op codes from program instruction register banks and/or receives those op codes and enables registers/arithmetic and logic operators to read/output values. In one or more embodiments, processing unit may include a floating-point unit (FPU) wherein the FPU is configured to handle arithmetic operations with floating point numbers. In one or more embodiments, processor 108 may include a plurality of processing units wherein each processing unit may be configured for a particular task and/or function. In one or more embodiments, each core within multi-core processor may function independently. In one or more embodiments, each core within multi-core processor may perform functions in parallel with other cores. In one or more embodiments, multi-core processor may allow for a dedicated core for each program and/or software running on a computing system. In one or more embodiments, multiple cores may be used for a singular function and/or multiple functions. In one or more embodiments, multi-core processor may allow for a computing system to perform differing functions in parallel. In one or more embodiments, processor 108 may include a plurality of multi-core processors. Computing device 104 may include any computing device as described in this disclosure, including without limitation a microcontroller, microprocessor, digital signal processor (DSP) and/or system on a chip (SoC) as described in this disclosure. Computing device 104 may include, be included in, and/or communicate with a mobile device such as a mobile telephone or smartphone. Computing device 104 may include a single computing device 104 operating independently or may include two or more computing devices operating in concert, in parallel, sequentially or the like; two or more computing devices may be included together in a single computing device 104 or in two or more computing devices. Computing device 104 may interface or communicate with one or more additional devices as described below in further detail via a network interface device. Network interface device may be utilized for connecting computing device 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device 104. Computing device 104 may include but is not limited to, for example, a computing device 104 or cluster of computing devices in a first location and a second computing device 104 or cluster of computing devices in a second location. Computing device 104 may include one or more computing devices dedicated to data storage, security, distribution of traffic for load balancing, and the like. Computing device 104 may distribute one or more computing tasks as described below across a plurality of computing devices of computing device 104, which may operate in parallel, in series, redundantly, or in any other manner used for distribution of tasks or memory 112 between computing devices. Computing device 104 may be implemented, as a non-limiting example, using a "shared nothing" architecture.

With continued reference to FIG. 1, computing device 104 may be designed and/or configured to perform any method, method step, or sequence of method steps in any embodiment described in this disclosure, in any order and with any degree of repetition. For instance, computing device 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computing device 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

With continued reference to FIG. 1, computing device 104 may perform determinations, classification, and/or analysis steps, methods, processes, or the like as described in this disclosure using machine-learning processes. A "machine-learning process," as used in this disclosure, is a process that automatedly uses a body of data known as "training data" and/or a "training set" (described further below in this disclosure) to generate an algorithm that will be performed by a Processor module to produce outputs given data provided as inputs; this is in contrast to a non-machine learning software program where the commands to be executed are determined in advance by a user and written in a programming language. A machine-learning process may utilize supervised, unsupervised, lazy-learning processes and/or neural networks, described further below.

With continued reference to FIG. 1, system 100 includes a memory 112 communicatively connected to processor 108, wherein the memory 112 contains instructions configuring processor 108 to perform any processing steps as described herein. As used in this disclosure, "communicatively connected" means connected by way of a connection, attachment, or linkage between two or more relata which allows for reception and/or transmittance of information therebetween. For example, and without limitation, this connection may be wired or wireless, direct, or indirect, and between two or more components, circuits, devices, systems, and the like, which allows for reception and/or transmittance of data and/or signal(s) therebetween. Data and/or signals therebetween may include, without limitation, electrical, electromagnetic, magnetic, video, audio, radio, and microwave data and/or signals, combinations thereof, and the like, among others. A communicative connection may be achieved, for example and without limitation, through wired or wireless electronic, digital, or analog, communication, either directly or by way of one or more intervening devices or components. Further, communicative connection may include electrically coupling or connecting at least an output of one device, component, or circuit to at least an input of another device, component, or circuit. For example, and without limitation, using a bus or other facility for intercommunication between elements of a computing device 104. Communicative connecting may also include indirect connections via, for example and without limitation, wireless connection, radio communication, low power wide area network, optical communication, magnetic, capacitive, or optical coupling, and the like. In some instances, the terminology "communicatively coupled" may be used in place of communicatively connected in this disclosure.

With continued reference to FIG. 1, memory 112 may include a primary memory and a secondary memory. "Primary memory" also known as "random access memory" (RAM) for the purposes of this disclosure is a short-term storage device in which information is processed. In one or more embodiments, during use of computing device 104, instructions and/or information may be transmitted to primary memory wherein information may be processed. In one or more embodiments, information may only be populated within primary memory while a particular software is running. In one or more embodiments, information within primary memory is wiped and/or removed after computing device 104 has been turned off and/or use of a software has been terminated. In one or more embodiments, primary memory may be referred to as "Volatile memory" wherein the volatile memory only holds information while data is being used and/or processed. In one or more embodiments, volatile memory may lose information after a loss of power. "Secondary memory" also known as "storage," "hard disk drive" and the like for the purposes of this disclosure is a long-term storage device in which an operating system and other information is stored. In one or remote embodiments, information may be retrieved from secondary memory and transmitted to primary memory during use. In one or more embodiments, secondary memory may be referred to as non-volatile memory wherein information is preserved even during a loss of power. In one or more embodiments, data within secondary memory cannot be accessed by processor. In one or more embodiments, data is transferred from secondary to primary memory wherein processor 108 may access the information from primary memory.

Still referring to FIG. 1, System 100 may include a database 116. Database may include a remote database 116. Database 116 may be implemented, without limitation, as a relational database, a key-value retrieval database such as a NOSQL database, or any other format or structure for use as database that a person skilled in the art would recognize as suitable upon review of the entirety of this disclosure. Database may alternatively or additionally be implemented using a distributed data storage protocol and/or data structure, such as a distributed hash table or the like. Database 116 may include a plurality of data entries and/or records as described above. Data entries in database may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries in database may store, retrieve, organize, and/or reflect data and/or records.

With continued reference to FIG. 1, system 100 may include and/or be communicatively connected to a server, such as but not limited to, a remote server, a cloud server, a network server and the like. In one or more embodiments. In one or more embodiments, computing device 104 may be configured to transmit one or more processes to be executed by server. In one or more embodiments, server may contain additional and/or increased processor power wherein one or more processes as described below may be performed by server. For example, and without limitation, one or more processes associated with machine learning may be performed by network server, wherein data is transmitted to server, processed and transmitted back to computing device. In one or more embodiments, server may be configured to perform one or more processes as described below to allow for increased computational power and/or decreased power usage by system computing device 104. In one or more embodiments, computing device 104 may transmit processes to server wherein computing device 104 may conserve power or energy.

With continued reference to FIG. 1, processor 108 is configured to receive user data 120 from a user. A "user" for the purposes of this disclosure is an individual interacting with system 100. In one or more embodiments, user may include an individual seeking rehabilitation, an individual seeking treatment and/or any other individuals who may interact with system 100. "User data" For the purposes of this disclosure is information about user. For example, and without limitation, user data 120 may include information about a user such as but not limited to, age name, gender, heigh weight and the like. In one or more embodiments, user data 120 may include information such as but not limited to age, geographic location, religious orientation, religious observance, sexual orientation, weight, physical activity, current diet, salary, employment history, educational history and the like. In one or more embodiments, user data 120 may include medical information associated with user such as but not limited to, medications taken treatments received, current diagnosis, genetic history and the like. In one or more embodiments, user data 120 may include any information needed to make one or more determinations about user as described in this disclosure. In one or more embodiments, user data 120 may be received through user input 124 through one or more remote devices and/or input devices, such as but not limited to a smartphone, laptop, desktop computer, wearable smart watch and the like.

With continued reference to FIG. 1, user data 120 may be associated with at least a neurological behavior 128. A "neurological behavior" or the purposes of this disclosure is an action that is affected by the nervous system, particularly the brain. For example and without limitation, neurological behavior 128 may include reflexes wherein an individual's automatic responses may be affected by stimuli. In one or more embodiments, neurological behavior 128 may include language and speech such as speaking or reading. In one or more embodiments, neurological behavior 128 may include learning and memory wherein learning and memory may include the formation of memories or the retrieval or memories. In one or more embodiments, neurological behavior 128 may include emotions wherein emotions may be affect by an individual's nervous system. In one or more embodiments, neurological behavior 128 may include sleep and wakefulness wherein the ability to sleep and/or the ability to transition between sleep patterns or cycles may be affect by the nervous system. In one or more embodiments, neurological behavior 128 may include social behaviors such as but not limited social interactions, feelings of sympathy, feelings of empathy and the like. In one or more embodiments, neurological behaviors 128 may include disorders, such as depression anxiety, bipolar disorders and the like. In one or more embodiments, neurological behavior 128 may include addition wherein the brain's reward system may be affect and as a result lead to compulsive behaviors. In one or more embodiments, addition may lead to changes in neurotransmitter levels and neural pathways. In one or more embodiments, neurological behavior 128 may include habits wherein habits may cause neural pathways to be strengthened through repeated actions. In one or more embodiments, habits may cause behavior to become more automatic and ingrained such that actions may be done unconsciously. In one or more embodiments, neurological behavior 128 may include a habitual deficiency. A "habitual deficiency" for the purposes of this disclosure is a neurological behavior 128 affects a user's ability to form or maintain a habit. For example, and without limitation, habitual deficiency may include the failure to maintain a particular diet, failure to adhere to sleep schedules, failure to adhere to exercise schedule, failure to adhere to a given set of tasks and the like. In one or more embodiments, habitual deficiency may refer to a habit that has not yet been formed and/or has not yet been fully formed. In one or more embodiments, user may contain a habitual deficiency such that they lack a particular habit that is sought to be desired. In one or more embodiments, a lacked habit may affect neurological behavior 128 wherein actions may not be affected by the nervous system, and as a result, such actions may not be taken. In one or more embodiments, user data 120 may include information associated with a neurological behavior 128 such as habitual deficiency wherein a user may include a habit that the user has failed to create or may include a habit that has not been fully created yet. In one or more embodiments, information associated with neurological behaviors 128 may include information such as, but not limited to, information associated with the neurological behavior 128 itself, information associated with an individual's brain activity, information associated with a user's sleep patterns, and the like.

With continued reference to FIG. 1, habitual deficiency may affect one or more life domains. A "life domain" as described herein refers to various aspects of life in which individuals experience and grow through. For example, and without limitation, life domain may include a marriage domain wherein an individual may experience marriage and companionship. In one or more embodiments, habitual deficiency may include an indication that a person is lacking a formed habit in one or more domains. In one or more embodiments, habitual deficiency may include information indicating that an individual would like to form a habit in one or more domains. In one or more embodiments, life domains may include one or more domains. In one or more embodiments, domains may include but are not limited to, vocational, marriage, family, health, virtue, emotional, financial, spiritual, intellectual, lifestyle, interest, and social to name a few. Each domain may have a status. Exemplary, non-limiting statuses include breakthrough, emerging, growth, plateau, stagnation, and depletion to name a few. In some cases, a domain status may be determined according to one or more state variables. State variable may be affected by objective data and/or subjective data. In one or more embodiments, objective data and/or subjective data may be retrieved from user data as described above. Exemplary non-limiting examples of objective data include medical measurements, time spent on certain activities, events participated in, number of steps taken, and generally speaking anything that can be measured. In some cases, remote device may directly measure or infer objective data, for example remote device may measure number of steps taken by user, amount of screen time, and the like. Alternatively or additionally objective data may be input by user into remote device. For example, a user may include user weight, user blood pressure, or any other objective datum by way of remote device. In some cases, user may input subjective data, for example by way of remote device. Subjective data may include a numerical representation (e.g., 1-10 rating) of how a user thinks or feels about a current aspect relating to a domain. For example, and without limitation, a user may rate a level of anxiety, a level of fulfillment, or the like. In an embodiment, one or more domains may be selected and/or isolated by a user. This may allow for a more focused and concentrated experience on one or more domains of interest to a user. In an embodiment, a user may select one or more domains to isolate and/or focus on. In yet another non-limiting example, computing device 104 may select one or more domains for a user to focus on, using a selection process that may include one or more machine learning processes as described throughout this application.

With continued reference to FIG. 1, at least a domain may include vocational domain. Objective data that may be associated with vocational domain includes title, role, responsibility, compensation, and the like. Subjective data may include a rating of user's level of vocational fulfillment. A domain target associated with vocational domain may include a change in a subjective or objective datum associated with the vocational domain. Schedule components or events that may be added to exploit value in vocational domain include professional training events, maximizing contribution, exploiting opportunities, and the like.

With continued reference to FIG. 1, at least a domain may include marriage domain. Objective data that may be associated with marriage domain includes amount of time spent with spouse, for example time spent enjoying one another. Subjective data may include a rating of user's level of marriage fulfillment. A domain target associated with marriage domain may include a change in a subjective or objective datum associated with the marriage domain. Schedule components or events that may be added to exploit value in marriage domain include events determined to maximize marriage fulfillment, including participating in couple centric events, self-sacrificial acts of love, couples therapy, honest communication sessions, and the like.

With continued reference to FIG. 1, at least a domain may include family domain. Objective data that may be associated with family domain includes amount of time spent with family. Subjective data may include a rating of user's level of family fulfillment or a rating of a family member's level of fulfillment with user/spouse. A domain target associated with family domain may include a change in a subjective or objective datum associated with the family domain. Schedule components or events that may be added to exploit value in family domain include events determined to maximize family fulfillment, including participating in family events, self-sacrificing acts of love, generosity of time, money, and service, and the like.

With continued reference to FIG. 1, at least a domain may include health domain. Objective data that may be associated with health domain includes medical data, such as without limitation body mass index, blood pressure, resting heart rate, blood oxygen content, and the like. Subjective data may include a rating of user's level of health fulfillment, a rating of number of activities a user feels are impaired by health concerns, a rating of overall concern with health, and the like. A domain target associated with health domain may include a change in a subjective or objective datum associated with the health domain. Schedule components or events that may be added to exploit value in health domain include events determined to maximize health fulfillment, exercise, nutritional meals, visits to medical professionals, and the like.

With continued reference to FIG. 1, at least a domain may include virtue domain. Objective data that may be associated with virtue domain includes amount of time acting virtuously, proportion of big decisions which are aligned with desirable virtues, amount of success or failure living within targeted virtue levels, evidence of retained or unretained resolve, and the like. Subjective data may include a rating of user's self-perceived level of virtue or a rating of user's perceived level of virtue from another. A domain target associated with virtue domain may include a change in a subjective or objective datum associated with the virtue domain. Schedule components or events that may be added to exploit value in virtue domain include events determined to maximize virtue fulfillment, including participating habit building exercises designed to facilitate consistently good decision making.

With continued reference to FIG. 1, at least a domain may include emotional domain. Objective data that may be associated with emotional domain includes amount of time spent in a state of emotional destress, amount of time in emotional harmony, amount of time sleeping, caloric intake, amount of time engaged in anxiety about the past or imagined future, and the like. Subjective data may include a rating of user's level of emotional fulfillment. A domain target associated with emotional domain may include a change in a subjective or objective datum associated with the emotional domain. Schedule components or events that may be added to exploit value in emotional domain include therapy, treatment under the supervision of health care professionals, events and exercises that are likely to improve a user's emotions, and the like.

With continued reference to FIG. 1, at least a domain may include financial domain. Objective data that may be associated with financial domain includes amount of financial assets possessed by user. Subjective data may include a rating of user's sense of financial security, independence and freedom. A domain target associated with financial domain may include a change in a subjective or objective datum associated with the financial domain. Schedule components or events that may be added to exploit value in financial domain include meeting with a financial advisor, increasing savings contributions, budgeting, and the like.

With continued reference to FIG. 1, at least a domain may include intellectual domain. Objective data that may be associated with intellectual domain includes amount performance in intellectual pursuits, such as graded performance in school. Subjective data may include a rating of user's level of intellectual fulfillment. A domain target associated with intellectual domain may include a change in a subjective or objective datum associated with the intellectual domain. Schedule components or events that may be added to exploit value in intellectual domain include events determined to maximize intellectual fulfillment, including enrolling in educational programs, enjoying cultural events, and the like.

With continued reference to FIG. 1, at least a domain may include lifestyle domain. Objective data that may be associated with lifestyle domain includes amount of time spent in ideal or unideal lifestyle settings. Subjective data may include a rating of user's level of lifestyle fulfillment. A domain target associated with lifestyle domain may include a change in a subjective or objective datum associated with the lifestyle domain. Schedule components or events that may be added to exploit value in lifestyle domain include events determined to maximize lifestyle fulfillment, including housing, travel, wardrobe, toys, activities, groups and free time.

With continued reference to FIG. 1, at least a domain may include interest domain. Objective data that may be associated with interest domain includes amount of time on avocational pursuits or personally enjoyable activities. Subjective data may include a rating of user's level of interest fulfillment. A domain target associated with interest domain may include a change in a subjective or objective datum associated with the interest domain. Schedule components or events that may be added to exploit value in interest domain include events determined to maximize interest fulfillment, including hobbyist events, and the like.

With continued reference to FIG. 1, at least a domain may include social domain. Objective data that may be associated with social domain includes amount of time spent with others in a social setting, for example time spent enjoying one another. Subjective data may include a rating of user's level of social fulfillment. A domain target associated with social domain may include a change in a subjective or objective datum associated with the social domain. Schedule components or events that may be added to exploit value in social domain include events determined to maximize social fulfillment, including participating in social events, engaging with a club, friends, groups, entertainment events, and the like.

With continued reference to FIG. 1, habitual deficiency may be used to identify one or more domains in which a user would like to form a habit and grow within. For example, and without limitation, a user may seek to grow in a marriage domain, wherein the user may desire to cultivate habits that allow for increased marriage related activities. In one or more embodiments, domains may include deficiencies that a user wishes to improve upon. In one or more embodiments, domains may be received by a user wherein processor 108 may generate habituation programs as a result. In one or more embodiments, users may seek to find purpose and meaning in life and seek to align habits with life goals. In one or more embodiments, habitual deficiency may include habits in which a user would desire to create in order to align their habits with their life goals. In one or more embodiments, users may seek fulfillment and/or purpose in life wherein a user may seek to create habits that would contribute to fulfillment and purpose. In one or more embodiments, creating habits may affect neurological behavior as the brain may alter habit formation and motor controls in order to create and/or break habits. In one or more embodiments, a user may seek to improve in one or more domains as described above, wherein habitual deficiency may include domains in which a user seeks to create a habit in. In one or more embodiments, the processor of habit formation may affect neurological behavior wherein neural connections may be strengthen and thereby lead to more efficient signaling pathways. Domain may include any domain described in this disclosure, including those described with reference to FIG. 2.

With continued reference to FIG. 1, user data 120 may include information relating to habits that the user may need to align with to achieve flourishment in selected areas. This information may include neurological information that helps an individual form a habit, maintain a habit, and the like. In one or more embodiments, neurological information may include which area of the brain is impacted by the selected habit and/or area of flourishment. In one or more embodiments, user data 120 may include information on how the user is customed to dealing with a neurological behavior 128. This may include information such as but not limited to, actions such as exercise, lifestyle choice, sleep, lack of sleep, reading, writing, and the like.

With continued reference to FIG. 1, user data 120 may include neurological information associated with the user. This may include but is not limited to, information associate with neurological activity such as brainwaves, and the like. In one or more embodiments, user data 120 may include information that can be deduced to determine neurological information about user. This may include, but is not limited to brain wave activity, sleep patterns, blood oxygen levels, heart rate data 176 and the like. In one or more embodiments, user data 120 may include a previous physiological response 172 and/or a plurality of previous physiological responses 172. This may be explained in further detail below.

With continued reference to FIG. 1, user data 120 may be received from a user through an input device. In one or more embodiments, input devices may include but are not limited to, devices such as smartphones, laptops, tablets, desktop computers, smart watches, smart glasses, augmented reality devices and the like. In one or more embodiments, user data 120 may be received through a user interface such as graphical user interface as described in further detail below. In one or more embodiments, user data 120 may be received through a chatbot wherein the chatbot may be configured to request data through interactive questions. A "chatbot system" for the purposes of this disclosure is a program configured to simulate human interaction with a user in order to receive or convey information. In some cases, chatbot system 132 may be configured to receive user data 120 and/or elements thereof and any other data as described in this disclosure through interactive questions presented to the user. In one or more embodiments, chatbot system 132 may be configured to simulate human interaction wherein chatbot system 132 may present questions in responses in a natural language format. In one or more embodiments, inputs by the user may also be received in a natural language format wherein chatbot system 132 may be configured to convert the inputs into computer languages. In one or more embodiments, chatbot system 132 may be configured to simulate human interaction in a variety of languages based on the preferences of a user. In one or more embodiments, while data processing and/or information received may be in a particular language, chatbot may be configured to translate data based on the preferences of the user. In one or more embodiment, chatbot may be configured to engage in passive data monitoring wherein a user's interactions with chatbot system 132 and/or computing device 104 may be recorded inexplicitly. For example, and without limitation, chatbot system 132 may present prompts to a user wherein chatbot system 132 may record the user's reaction time, the user's choice of words, the user's attention to detail in the answers and the like. In one or more embodiments, chatbot system 132 may be configured to record actions or behaviors that a user unconsciously exhibits for use in user data 120.

With continued reference to FIG. 1, user data 120 may be received from one or more sensors. In one or more embodiments, input device may include one or more sensors, wherein user data 120 may be received. In one or more embodiments, processor 108 may be configured to iteratively receive user data 120 from one or more sensors. For example, and without limitation, processor 108 may be configured to receive blood oxygen levels from an oxygen sensor, heart rate levels from a heart rate sensor and the like. In one or more embodiments, sensors may be physically connected to user throughout one or more hours of a day, wherein processor 108 may be configured to receive elements of user data 120. In one or more embodiments, input device may include a wearable device such as a smartwatch. In one or more embodiments, the wearable device may contain one or more sensors configured to receive location, oxygen levels, heart rate levels and the like.

With continued reference to FIG. 1, sensor 136 may include one or more sensors. As used in this disclosure, a "sensor" is a device that is configured to detect an input and/or a phenomenon and transmit information related to the detection. For example, and without limitation, a sensor may transduce a detected charging phenomenon and/or characteristic, such as, and without limitation, temperature, voltage, current, pressure, and the like, into a sensed signal such as a voltage with respect to a reference. Sensor 136 may detect a plurality of data. A plurality of data detected by sensor 136 may include, but is not limited to, heart rate, blood oxygen levels, temperature, moisture level, and the like. In one or more embodiments, and without limitation, sensor 136 may include a plurality of sensors. In one or more embodiments, and without limitation, sensor 136 may include an optical or image sensor such as a camera, a CMOS detector, a CCD detector, a video camera, a photodiode, a photovoltaic cell, a photoconductive device, a thermal and/or infrared camera, one or more temperature sensors, voltmeters, current sensors, hydrometers, infrared sensors, photoelectric sensors, ionization smoke sensors, motion sensors, pressure sensors, radiation sensors, level sensors, imaging devices, moisture sensors, gas and chemical sensors, flame sensors, electrical sensors, imaging sensors, force sensors, Hall sensors, and the like. Sensor may be a contact or a non-contact sensor. Signals may include electrical, electromagnetic, visual, audio, radio waves, or another undisclosed signal type alone or in combination.

With continued reference to FIG. 1, sensor 136 may include a plurality of independent sensors, where any number of the described sensors may be used to detect any number of physical or quantities associated with a user. Independent sensors may include separate sensors measuring physical quantities that may be powered by and/or in communication with circuits independently, where each may sensor 136 output to a control circuit such as a user graphical interface. In an embodiment, use of a plurality of independent sensors may result in redundancy configured to employ more than one sensor 136 that measures the same phenomenon, those sensors being of the same type, a combination of, or another type of sensor 136 not disclosed, so that in the event one sensor 136 fails, the ability of sensor 136 to detect phenomenon may be maintained.

With continued reference to FIG. 1, sensor 136 may include a plurality of sensing devices, such as, but not limited to, temperature sensors, humidity sensors, accelerometers, electrochemical sensors, gyroscopes, magnetometers, inertial measurement unit (IMU), pressure sensor, proximity sensor, displacement sensor, force sensor, vibration sensor, heart rate monitor, blood oxygen level monitor, blood pressure monitor and the like. Sensor may be configured to detect a plurality of data, as discussed further below in this disclosure. A plurality of data may be detected from sensor.

With continued reference to FIG. 1 sensor 136 may include a sense board. A sense board may have at least a portion of a circuit board that includes one or more sensors configured to measure or detect a sensor 136 input. In one or more embodiments, a sense board may include one or more circuits and/or circuit elements, including, for example, a printed circuit board component. A sense board may include, without limitation, a control circuit configured to perform and/or direct any actions performed by the sense board and/or any other component and/or element described in this disclosure. The control circuit may include any analog or digital control circuit, including without limitation a combinational and/or synchronous logic circuit, a processor 108, microprocessor, microcontroller, or the like.

With continued reference to FIG. 1, sensor 136 is configured to transmit a sensor 136 output signal representative of sensed information. As used in this disclosure, a "sensor 136 signal" is a representation of a sensed information that sensor 136 may generate. A sensor 136 signal may include any signal form described in this disclosure, for example digital, analog, optical, electrical, fluidic, and the like. In some cases, a sensor 136, a circuit, and/or a controller may perform one or more signal processing steps on a signal. For instance, sensor 136, circuit, and/or controller may analyze, modify, and/or synthesize a signal in order to improve the signal, for instance by improving transmission, storage efficiency, or signal to noise ratio.

With continued reference to FIG. 1, exemplary methods of signal processing may include analog, continuous time, discrete, digital, nonlinear, and statistical. Analog signal processing may be performed on non-digitized or analog signals. Exemplary analog processes may include passive filters, active filters, additive mixers, integrators, delay lines, compandors, multipliers, voltage-controlled filters, voltage-controlled oscillators, and phase-locked loops. Continuous-time signal processing may be used, in some cases, to process signals which varying continuously within a domain, for instance time. Exemplary non-limiting continuous time processes may include time domain processing, frequency domain processing (Fourier transform), and complex frequency domain processing. Discrete time signal processing may be used when a signal is sampled non-continuously or at discrete time intervals (i.e., quantized in time). Analog discrete-time signal processing may process a signal using the following exemplary circuits sample and hold circuits, analog time-division multiplexers, analog delay lines and analog feedback shift registers. Digital signal processing may be used to process digitized discrete-time sampled signals. Commonly, digital signal processing may be performed by a computing device 104 or other specialized digital circuits, such as without limitation an application specific integrated circuit (ASIC), a field-programmable gate array (FPGA), or a specialized digital signal processor (DSP). Digital signal processing may be used to perform any combination of typical arithmetical operations, including fixed-point and floating-point, real-valued and complex-valued, multiplication and addition. Digital signal processing may additionally operate circular buffers and lookup tables. Further non-limiting examples of algorithms that may be performed according to digital signal processing techniques include fast Fourier transform (FFT), finite impulse response (FIR) filter, infinite impulse response (IIR) filter, and adaptive filters such as the Wiener and Kalman filters. Statistical signal processing may be used to process a signal as a random function (i.e., a stochastic process), utilizing statistical properties. For instance, in some embodiments, a signal may be modeled with a probability distribution indicating noise, which then may be used to reduce noise in a processed signal.

With continued reference to FIG. 1, a wearable device such as smartwatch may include one or more sensors, wherein the one or more sensors may include heart rate monitors, oxygen level monitors, blood pressure monitors and the like.

With continued reference to FIG. 1, processor 108 is configured to generate a habituation program 140. A "habituation program" for the purposes of this disclosure is a treatment for the neurological behavior 128 indicated within user data 120. For example, and without limitation, habituation program may include treatments to reduce depression, treatments to help with social anxiety, treatment with eating disorders and the like. In one or more embodiments, habituation program 140 may include a series of steps or instructions that would inform user on how to treat neurological behavior 128. This may include instructions to remedy a bad habit, instructions to improve sleep quality, instructions to improve social anxiety and the like. In one or more embodiments, habituation program 140 may include steps or instructions that are configured for user data 120, such as but not limited to instructions associated with a user's geographic location, instructions associated with a user's religious belief, instructions associated with a user's weight, instructions associated with a user's lifestyle choice and the like. In one or more embodiments, habituation program 140 may seek to improve one or more elements of a user's lifestyle in order to treat the neurological behavior 128 requiring attention. In one or more embodiments, processor 108 may use user data 120 and determine which aspects of a user's lifestyle may require attention in order to treat neurological behavior 128. In one or more embodiments, habituation program 140 may be geared based on a user's dietary restrictions, based on a user's procession, based on what tools are available to the user to utilize and the like.

With continued reference to FIG. 1, processor 108 is configured to generate a habituation program 140 as a function of the user data 120 and a machine learning process. In one or more embodiments, computing device 104 may include a machine learning module to implement one or more algorithms or generate one or more machine-learning models to generate outputs. However, the machine learning module is exemplary and may not be necessary to generate one or more machine learning models and perform any machine learning described herein. In one or more embodiments, one or more machine-learning models may be generated using training data. Training data may include inputs and corresponding predetermined outputs so that a machine-learning model may use correlations between the provided exemplary inputs and outputs to develop an algorithm and/or relationship that then allows machine-learning model to determine its own outputs for inputs. Training data may contain correlations that a machine-learning process may use to model relationships between two or more categories of data elements. Exemplary inputs and outputs may come from database 116, user inputs 124 and/or be provided by a user. In other embodiments, a machine-learning module may obtain a training set by querying a communicatively connected database 116 that includes past inputs and outputs. Training data may include inputs from various types of databases 116, resources, libraries, dependencies and/or user inputs 124 and outputs correlated to each of those inputs so that a machine-learning model may determine an output. Correlations may indicate causative and/or predictive links between data, which may be modeled as relationships, such as mathematical relationships, by machine-learning models, as described in further detail below. In one or more embodiments, training data may be formatted and/or organized by categories of data elements by, for example, associating data elements with one or more descriptors corresponding to categories of data elements. As a non-limiting example, training data may include data entered in standardized forms by persons or processes, such that entry of a given data element in a given field in a form may be mapped to one or more descriptors of categories. Elements in training data may be linked to categories by tags, tokens, or other data elements. A machine learning module may be used to create a machine learning model and/or any other machine learning model using training data. Training data may be data sets that have already been converted from raw data whether manually, by machine, or any other method. In some cases, the machine learning model may be trained based on user input 124. For example, a user may indicate that information that has been output is inaccurate wherein the machine learning model may be trained as a function of the user input 124. In some cases, the machine learning model may allow for improvements to computing device 104 such as but not limited to improvements relating to comparing data items, the ability to sort efficiently, an increase in accuracy of analytical methods and the like.

With continued reference to FIG. 1, in one or more embodiments, a machine-learning module may be generated using training data. Training data may include inputs and corresponding predetermined outputs so that machine-learning module may use the correlations between the provided exemplary inputs and outputs to develop an algorithm and/or relationship that then allows machine-learning module to determine its own outputs for inputs. Training data may contain correlations that a machine-learning process may use to model relationships between two or more categories of data elements. The exemplary inputs and outputs may come from a database 116 and/or be provided by a user. In other embodiments, machine-learning module may obtain a training set by querying a communicatively connected database 116 that includes past inputs and outputs. Training data may include inputs from various types of databases 116, resources, libraries, dependencies and/or user inputs 124 and outputs correlated to each of those inputs so that a machine-learning module may determine an output. Correlations may indicate causative and/or predictive links between data, which may be modeled as relationships, such as mathematical relationships, by machine-learning processes, as described in further detail below. In one or more embodiments, training data may be formatted and/or organized by categories of data elements by, for example, associating data elements with one or more descriptors corresponding to categories of data elements. As a non-limiting example, training data may include data entered in standardized forms by persons or processes, such that entry of a given data element in a given field in a form may be mapped to one or more descriptors of categories.

With continued reference to FIG. 1, machine learning process may include habituation machine learning model 144. In one or more embodiments, habituation program 140 may be generated as function of habituation machine learning model 144. In one or more embodiments, habituation machine learning model 144 may be configured to receive inputs such as user data 120 and/or neurological behavior 128 and output habituation programs 140. In one or more embodiments, elements of user data 120 and a particular neurological behavior 128 may be associate with a particular habituation program 140. In one or more embodiments, habituation machine learning model 144 may receive user data 120 and/or neurological behavior 128 and output habituation program 140. In one or more embodiments. Habituation machine learning model 144 may be trained within habituation training data 148. In one or more embodiments, habituation training data 148 may include a plurality of user data 120 correlated to a plurality of user data 120 correlated to a plurality of habituation programs 140. In an embodiment, a particular set of user data 120 may be correlated to a particular habituation program 140. In an embodiment, an input such as user data 120 may be correlated to a habituation program 140 output. In one or more embodiments, habituation training data 148 may be received from a user, third party medical processional and the like. In one or more embodiments, habituation training data 148 may be initially created by a medical profession, wherein habituation machine learning model 144 may be iteratively trained based on feedback received on outputs. In an embodiment, habituation training data 148 may be limited in size and therefore a machine learning model such as habituation machine learning model 144 may struggle to generate outputs for unseen data. In one or more embodiments, a limited set of habituation training data 148 may cause low accuracy, higher error rates and/or other inaccurate outputs. In one or more embodiments, habituation machine learning model 144 may first be trained with a habituation training data 148 having a limited data set and iteratively trained using feedback from users on the accuracy of habituation program 140 outputs. In one or more embodiments, feedback may allow for habituation machine learning model 144 to be trained on a limited data set. In one or more embodiments, feedback may be used to increase the amount of inputs and correlated outputs by receiving user data 120, generating habituation programs 140 and receiving feedback on the habituation programs 140. In an embodiment, positive feedback may indicate that an input had a correct correlated output, while negative feedback may be used to indicate that an input may have not had a correct correlated outputs.

In one or more embodiments, a machine learning model such as habituation machine learning model 144 may contain parameter values 152. "Parameter values" for the purposes of this disclosure are internal variables that a machine learning model has generated from training data in order to make predictions. In one or more embodiments, parameter values 152 may include weights associated with a machine learning model wherein the weights may include coefficients used to calculate outputs for the machine learning model. In one or more embodiments, parameter values 152 may be adjusted during pretraining or training in order to minimize a loss function. In one or more embodiments, during training, predicted outputs of the machine learning model are compared to actual outputs wherein the discrepancy between predicted output and actual outputs are measured in order to minimize a loss function. A loss function also known an "error function" may measure the difference between predicted outputs and actual outputs in order to improve the performance of the machine learning model. A loss function may quantify the error margin between a predicted output and an actual output wherein the error margin may be sought to be minimized during the training process. The loss function may allow for minimization of discrepancies between predicted outputs and actual outputs of the machine learning model. In one or more embodiments, the loss function may adjust parameter values 152 of the machine learning model. In one or more embodiments, in a linear regression model, parameter values 152 may include coefficients assigned to each feature and the bias term. In one or more embodiments, in a neural network, parameter values 152 may include weights and biases associated with the connection between neurons or nodes within layers of the network. In one or more embodiments, during pretraining and/or training of the machine learning model, parameter values 152 of the machine learning model (e.g. Habituation machine learning model 144) may be adjusted as a function of habituation training data 148. In one or more embodiments, habituation machine learning model 144 may receive inputs within habituation training data 148 and predict outputs. In one or more embodiments, habituation machine learning model 144 may adjust parameter values 152 of the machine learning model based on a comparison between predicted outputs and actual outputs contained within habituation training data 148. In one or more embodiments, parameter values 152 may be adjusted to minimize a loss function such that a discrepancy between actual outputs and predicted outputs are minimized. In one or more embodiments, processor 108 may be configured to minimize a loss function by adjusting parameter values 152 of habituation machine learning model 144 based on discrepancies between predicted outputs and actual outputs as indicated within habituation training data 148. In one or more embodiments, training habituation machine learning model 144 may include adjusting one or more parameter values 152 of habituation machine learning model 144 as a function of a comparison between at least one predicted output and/or predicted habituation program 140 and at least one habituation program 140 contained within habituation training data 148. In one or more embodiments, processor 108 may be configured to iteratively train habituation machine learning model 144, wherein processor 108 may be configured to iteratively receive user data 120 from users, generate habituation program 140 and train the machine learning model based on feedback received from the output of habituation machine learning model 144. In an embodiment, the more positive feedback received from pairs of user data 120 and generated habituation programs 140 the more, the more accurate the Habituation machine learning model 144 may be in predicting future habituation programs 140.

With continued reference to FIG. 1, habituation machine learning model 144 may be iteratively trained receiving feedback data 156 and adjusting one or more parameter values 152 of habituation machine learning model 144 as a function of the feedback data 156. "Feedback data" for the purposes of this disclosure is information associated with the accuracy of an outputs of habituation machine learning model 144. For example, and without limitation, habituation machine learning model 144 may generate habituation program 140 for a user wherein user may provide input on whether the habituation program 140 was successful and/or whether the habituation was effective for the particular user. In one or more embodiments, user may indicate various elements of habituation program 140 that are incorrect or inapplicable to user. In one or more embodiments habituation program 140 may contain multiple steps and/or instructions wherein a user may indicate that a particular step or instruction was inaccurate. In one or more embodiments, habituation machine learning model 144 may be iteratively updated in order to properly correlate inputs and outputs. In one or more embodiments, parameter values 152 associated with habituation machine learning model 144 may be iteratively refined and/or updated in order to create more accurate outputs. In one or more embodiments, feedback from users may be used to train habituation machine learning model 144 in instances in which training data is limited. In one or more embodiments, feedback data 156 may allow for training in real time in which users may continuously provide feedback to habituation machine learning model 144 in order to receive more accurate results. In one or more embodiments, a user may interact with system 100 continuously and/or periodically wherein habituation machine learning model 144 may receive feedback on previously generated habituation programs 140 and output new habilitation programs based on feedback. In one or more embodiments, user data 120 may include previously generated habituation programs 140 wherein previously generated habituation programs 140 may include habituation programs 140 generated for use on a previous hour, day, month and the like. In one or more embodiments, habituation machine learning model 144 may receive habilitation programs previously generated and generate new habilitation programs as a function of feedback data 156. In one or more embodiments, chatbot system 132 may be configured to receive feedback data 156 wherein chatbot system 132 may ask questions such as but not limited to., "how have you enjoyed the habituation program 140 thus far?", "what steps of the habituation program 140 were easy for you and what steps where hard for you?" and the like. In one or more embodiments, chatbot system 132 may receive feedback data 156 in a natural language wherein natural language may include a form of communication made by humans. In one or more embodiments, chatbot system 132 and/or processor 108 may convert natural language into computer generated language wherein computer generated language may include communication made in a format readable by computing systems. In one or more embodiments chatbot system 132 may receive feedback data 156 by simulating human conversation and converting feedback data 156 into computer readable information. In one or more embodiments, feedback data 156 may be converted into Boolean values to indicate various issues with outputs and the like.

language model to receive information in the form of communication, such as but not limited to, user data 120 and/or feedback data 156 and convert the communication into o a format suitable for processing by processor 108 and/or a format suitable for habituation machine learning model 144 to generate outputs and/or to be iteratively trained. In one or more embodiments, user of system 100 may not understand how to train habituation machine learning model 144 but user may have feedback on the outputs. In an embodiment, chatbot system 132 and/or processor 108 may receive feedback and convert feedback into computer readable information that may be used to train habituation machine learning model 144 and/or that may be used to receive outputs from habituation machine learning model 144.

Still referring to FIG. 1, system 100 may include a large language model (LLM) and/or system 100 may be communicatively connected to large language model. In one or more embodiments, inputs into chatbot system 132 may be transmitted to LLM, wherein LLM may transmit back computer readable information. In one or more embodiments, LLM may further be used to simulate human interaction when receiving inputs such as user data 120 and/or feedback data 156. A "large language model," as used herein, is a deep learning data structure that can recognize, summarize, translate, predict and/or generate text and other content based on knowledge gained from massive datasets. Large language models may be trained on large sets of data. Training sets may be drawn from diverse sets of data such as, as non-limiting examples, novels, blog posts, articles, emails, unstructured data, electronic records, and the like. In some embodiments, training sets may include a variety of subject matters, such as, as nonlimiting examples, medical report documents, electronic health records, entity documents, business documents, inventory documentation, habituation programs 140, emails, user communications, advertising documents, newspaper articles, and the like. In some embodiments, training sets of an LLM may include information from one or more public or private databases 116. As a non-limiting example, training sets may include databases 116 associated with an entity. In some embodiments, training sets may include portions of documents associated with the electronic records correlated to examples of outputs. In an embodiment, an LLM may include one or more architectures based on capability requirements of an LLM. Exemplary architectures may include, without limitation, GPT (Generative Pretrained Transformer), BERT (Bidirectional Encoder Representations from Transformers), T5 (Text-To-Text Transfer Transformer), and the like. Architecture choice may depend on a needed capability such generative, contextual, or other specific capabilities.

With continued reference to FIG. 1, in some embodiments, an LLM may be generally trained. As used in this disclosure, a "generally trained" LLM is an LLM that is trained on a general training set comprising a variety of subject matters, data sets, and fields. In some embodiments, an LLM may be initially generally trained. Additionally, or alternatively, an LLM may be specifically trained. As used in this disclosure, a "specifically trained" LLM is an LLM that is trained on a specific training set, wherein the specific training set includes data including specific correlations for the LLM to learn. As a non-limiting example, an LLM may be generally trained on a general training set, then specifically trained on a specific training set. In an embodiment, specific training of an LLM may be performed using a supervised machine learning process. In some embodiments, generally training an LLM may be performed using an unsupervised machine learning process. As a non-limiting example, specific training set may include information from a database 116. As a non-limiting example, specific training set may include text related to the users such as user specific data for electronic records correlated to examples of outputs. In an embodiment, training one or more machine learning models may include setting the parameters of the one or more models (weights and biases) either randomly or using a pretrained model. Generally training one or more machine learning models on a large corpus of text data can provide a starting point for fine-tuning on a specific task. A model such as an LLM may learn by adjusting its parameters during the training process to minimize a defined loss function, which measures the difference between predicted outputs and ground truth. Once a model has been generally trained, the model may then be specifically trained to fine-tune the pretrained model on task-specific data to adapt it to the target task. Fine-tuning may involve training a model with task-specific training data, adjusting the model's weights to optimize performance for the particular task. In some cases, this may include optimizing the model's performance by fine-tuning hyperparameters such as learning rate, batch size, and regularization. Hyperparameter tuning may help in achieving the best performance and convergence during training. In an embodiment, fine-tuning a pretrained model such as an LLM may include fine-tuning the pretrained model using Low-Rank Adaptation (LoRA). As used in this disclosure, "Low-Rank Adaptation" is a training technique for large language models that modifies a subset of parameters in the model. Low-Rank Adaptation may be configured to make the training process more computationally efficient by avoiding a need to train an entire model from scratch. In an exemplary embodiment, a subset of parameters that are updated may include parameters that are associated with a specific task or domain.

With continued reference to FIG. 1, in some embodiments an LLM may include and/or be produced using Generative Pretrained Transformer (GPT), GPT-2, GPT-3, GPT-4, and the like. GPT, GPT-2, GPT-3, GPT-3.5, and GPT-4 are products of Open AI Inc., of San Francisco, CA. An LLM may include a text prediction based algorithm configured to receive an article and apply a probability distribution to the words already typed in a sentence to work out the most likely word to come next in augmented articles. For example, if some words that have already been typed are "Nice to meet", then it may be highly likely that the word "you" will come next. An LLM may output such predictions by ranking words by likelihood or a prompt parameter. For the example given above, an LLM may score "you" as the most likely, "your" as the next most likely, "his" or "her" next, and the like. An LLM may include an encoder component and a decoder component.

Still referring to FIG. 1, an LLM may include a transformer architecture. In some embodiments, encoder component of an LLM may include transformer architecture. A "transformer architecture," for the purposes of this disclosure is a neural network architecture that uses self-attention and positional encoding. Transformer architecture may be designed to process sequential input data, such as natural language, with applications towards tasks such as translation and text summarization. Transformer architecture may process the entire input all at once. "Positional encoding," for the purposes of this disclosure, refers to a data processing technique that encodes the location or position of an entity in a sequence. In some embodiments, each position in the sequence may be assigned a unique representation. In some embodiments, positional encoding may include mapping each position in the sequence to a position vector. In some embodiments, trigonometric functions, such as sine and cosine, may be used to determine the values in the position vector. In some embodiments, position vectors for a plurality of positions in a sequence may be assembled into a position matrix, wherein each row of position matrix may represent a position in the sequence.

With continued reference to FIG. 1, an LLM and/or transformer architecture may include an attention mechanism. An "attention mechanism," as used herein, is a part of a neural architecture that enables a system to dynamically quantify the relevant features of the input data. In the case of natural language processing, input data may be a sequence of textual elements. It may be applied directly to the raw input or to its higher-level representation.

With continued reference to FIG. 1, attention mechanism may represent an improvement over a limitation of an encoder-decoder model. An encoder-decider model encodes an input sequence to one fixed length vector from which the output is decoded at each time step. This issue may be seen as a problem when decoding long sequences because it may make it difficult for the neural network to cope with long sentences, such as those that are longer than the sentences in the training corpus. Applying an attention mechanism, an LLM may predict the next word by searching for a set of positions in a source sentence where the most relevant information is concentrated. An LLM may then predict the next word based on context vectors associated with these source positions and all the previously generated target words, such as textual data of a dictionary correlated to a prompt in a training data set. A "context vector," as used herein, are fixed-length vector representations useful for document retrieval and word sense disambiguation.

Still referring to FIG. 1, attention mechanism may include, without limitation, generalized attention self-attention, multi-head attention, additive attention, global attention, and the like. In generalized attention, when a sequence of words or an image is fed to an LLM, it may verify each element of the input sequence and compare it against the output sequence. Each iteration may involve the mechanism's encoder capturing the input sequence and comparing it with each element of the decoder's sequence. From the comparison scores, the mechanism may then select the words or parts of the image that it needs to pay attention to. In self-attention, an LLM may pick up particular parts at different positions in the input sequence and over time compute an initial composition of the output sequence. In multi-head attention, an LLM may include a transformer model of an attention mechanism. Attention mechanisms, as described above, may provide context for any position in the input sequence. For example, if the input data is a natural language sentence, the transformer does not have to process one word at a time. In multi-head attention, computations by an LLM may be repeated over several iterations, each computation may form parallel layers known as attention heads. Each separate head may independently pass the input sequence and corresponding output sequence element through a separate head. A final attention score may be produced by combining attention scores at each head so that every nuance of the input sequence is taken into consideration. In additive attention (Bahdanau attention mechanism), an LLM may make use of attention alignment scores based on a number of factors. Alignment scores may be calculated at different points in a neural network, and/or at different stages represented by discrete neural networks. Source or input sequence words are correlated with target or output sequence words but not to an exact degree. This correlation may take into account all hidden states and the final alignment score is the summation of the matrix of alignment scores. In global attention (Luong mechanism), in situations where neural machine translations are required, an LLM may either attend to all source words or predict the target sentence, thereby attending to a smaller subset of words.

With continued reference to FIG. 1, multi-headed attention in encoder may apply a specific attention mechanism called self-attention. Self-attention allows models such as an LLM or components thereof to associate each word in the input, to other words. As a non-limiting example, an LLM may learn to associate the word "you", with "how" and "are". It's also possible that an LLM learns that words structured in this pattern are typically a question and to respond appropriately. In some embodiments, to achieve self-attention, input may be fed into three distinct fully connected neural network layers to create query, key, and value vectors. Query, key, and value vectors may be fed through a linear layer; then, the query and key vectors may be multiplied using dot product matrix multiplication in order to produce a score matrix. The score matrix may determine the amount of focus for a word should be put on other words (thus, each word may be a score that corresponds to other words in the time-step). The values in score matrix may be scaled down. As a non-limiting example, score matrix may be divided by the square root of the dimension of the query and key vectors. In some embodiments, the softmax of the scaled scores in score matrix may be taken. The output of this softmax function may be called the attention weights. Attention weights may be multiplied by your value vector to obtain an output vector. The output vector may then be fed through a final linear layer.

Still referencing FIG. 1, in order to use self-attention in a multi-headed attention computation, query, key, and value may be split into N vectors before applying self-attention. Each self-attention process may be called a "head." Each head may produce an output vector and each output vector from each head may be concatenated into a single vector. This single vector may then be fed through the final linear layer discussed above. In theory, each head can learn something different from the input, therefore giving the encoder model more representation power.

With continued reference to FIG. 1, encoder of transformer may include a residual connection. Residual connection may include adding the output from multi-headed attention to the positional input embedding. In some embodiments, the output from residual connection may go through a layer normalization. In some embodiments, the normalized residual output may be projected through a pointwise feed-forward network for further processing. The pointwise feed-forward network may include a couple of linear layers with a ReLU activation in between. The output may then be added to the input of the pointwise feed-forward network and further normalized.

Continuing to refer to FIG. 1, transformer architecture may include a decoder. Decoder may a multi-headed attention layer, a pointwise feed-forward layer, one or more residual connections, and layer normalization (particularly after each sub-layer), as discussed in more detail above. In some embodiments, decoder may include two multi-headed attention layers. In some embodiments, decoder may be autoregressive. For the purposes of this disclosure, "autoregressive" means that the decoder takes in a list of previous outputs as inputs along with encoder outputs containing attention information from the input.

With further reference to FIG. 1, in some embodiments, input to decoder may go through an embedding layer and positional encoding layer in order to obtain positional embeddings. Decoder may include a first multi-headed attention layer, wherein the first multi-headed attention layer may receive positional embeddings.

With continued reference to FIG. 1, first multi-headed attention layer may be configured to not condition to future tokens. As a non-limiting example, when computing attention scores on the word "am," decoder should not have access to the word "fine" in "I am fine," because that word is a future word that was generated after. The word "am" should only have access to itself and the words before it. In some embodiments, this may be accomplished by implementing a look-ahead mask. Look ahead mask is a matrix of the same dimensions as the scaled attention score matrix that is filled with "0s" and negative infinities. For example, the top right triangle portion of look-ahead mask may be filled with negative infinities. Look-ahead mask may be added to scaled attention score matrix to obtain a masked score matrix. Masked score matrix may include scaled attention scores in the lower-left triangle of the matrix and negative infinities in the upper-right triangle of the matrix. Then, when the softmax of this matrix is taken, the negative infinities will be zeroed out; this leaves zero attention scores for "future tokens".

Still referring to FIG. 1, second multi-headed attention layer may use encoder outputs as queries and keys and the outputs from the first multi-headed attention layer as values. This process matches the encoder's input to the decoder's input, allowing the decoder to decide which encoder input is relevant to put a focus on. The output from second multi-headed attention layer may be fed through a pointwise feedforward layer for further processing.

With continued reference to FIG. 1, the output of the pointwise feedforward layer may be fed through a final linear layer. This final linear layer may act as a classifier. This classifier may be as big as the number of classes that you have. For example, if you have 10,000 classes for 10,000 words, the output of that classifier will be of size 10,000. The output of this classifier may be fed into a softmax layer which may serve to produce probability scores between zero and one. The index may be taken of the highest probability score in order to determine a predicted word.

Still referring to FIG. 1, decoder may take this output and add it to the decoder inputs. Decoder may continue decoding until a token is predicted. Decoder may stop decoding once it predicts an end token.

Continuing to refer to FIG. 1, in some embodiment, decoder may be stacked N layers high, with each layer taking in inputs from the encoder and layers before it. Stacking layers may allow an LLM to learn to extract and focus on different combinations of attention from its attention heads.

With continued reference to FIG. 1, an LLM may receive an input. Input may include a string of one or more characters. Inputs may additionally include unstructured data. For example, input may include one or more words, a sentence, a paragraph, a thought, a query, and the like. A "query" for the purposes of the disclosure is a string of characters that poses a question. In some embodiments, input may be received from a user device. User device may be any computing device 104 that is used by a user. As non-limiting examples, user device may include desktops, laptops, smartphones, tablets, and the like. In some embodiments, input may include any set of data associated with system 100 such as but not limited to user data 120 and/or feedback data 156 wherein outputs may include information within a computer language format. Additionally or alternatively, system 100 and/or habituation machine learning model 144 may generate information within a computer language format wherein information may be translated by LLM into a natural language format for the user to understand.

With continued reference to FIG. 1, an LLM may generate at least one annotation as an output. At least one annotation may be any annotation as described herein. In some embodiments, an LLM may include multiple sets of transformer architecture as described above. Output may include a textual output. A "textual output," for the purposes of this disclosure is an output comprising a string of one or more characters. Textual output may include, for example, a plurality of annotations for unstructured data. In some embodiments, textual output may include a phrase or sentence identifying the status of a user query. In some embodiments, textual output may include a sentence or plurality of sentences describing a response to a user query. As a non-limiting example, this may include restrictions, timing, advice, dangers, benefits, and the like.

With continued reference to FIG. 1, processor 108 may generate habituation program 140 as a function of habituation machine learning model 144. In one or more embodiments, processor 108 may first receive neurological behavior 128 and classify neurological behavior 128 to a neurological class. A "neurological class" for the purposes of this disclosure is a grouping of neurological behaviors 128. For example, and without limitation, neurological class 160 may include a grouping of neurological behaviors 128 associated with social anxiety, a grouping of neurological behaviors 128 associated with sleep issues, a grouping of neurological behaviors 128 associated with habit formation or removal, a grouping of neurological behaviors 128 associated with dieting, a grouping of neurological behaviors 128 associated with addiction and the like. In one or more embodiments, each neurological behaviors 128 may be correlated and/or belong to a particular neurological grouping wherein processor 108 may first determine which neurological grouping, neurological behavior 128 belongs to. In one or more embodiments, processor 108 may first be configured to classify neurological behavior 128 to a neurological grouping using a classification algorithm and/or a machine learning model as described in this disclosure. In one or more embodiments, computing device 104 may utilize a machine learning model to classify neurological behavior 128 to one or more neurological classes 160. The machine learning model may include any machine learning model as described in this disclosure. Processor 108 may use a machine learning module, such as a classifier machine learning module for the purposes of this disclosure, to implement one or more algorithms or generate one or more machine-learning models, such as a classifier machine learning model to classify one or more neurological behaviors 128. In one or more embodiments, training data for classifier machine learning model may include neurological behaviors 128 with labels indicating neurological classes 160. In one or more embodiments, processor 108 may be configured to classify neurological behavior 128 to neurological class 160 and generate habitability program as a function of the classification. In one or more embodiments, classified neurological behavior 128 may be input into habituation machine learning model 144 wherein habituation machine learning model 144 may generate habituation program 140. In one or more embodiments, habituation training data 148 may be separated and/or classified into neurological classes 160 wherein a particular input classified to a neurological class 160 may be correlated to an output classified to the same class. In one or more embodiments, classifying habituation training data 148 may allow for outputs with increased accuracy wherein inputs and correlated outputs are classified to the same grouping. In one or more embodiments, processor 108 may use a lookup table and/or query a database 116 as a function of the classification wherein database 116 and/or lookup table may contain habituation programs 140 for each corresponding neurological class 160.

With continued reference to FIG. 1, processor 108 is configured to track a user's adaptability to habituation program 140. In one or more embodiments, the tracking of user's adaptability to habituation program 140 may be recorded as adaptability data 164. "Adaptability data" or "the user's adaptability to habituation program" for the purposes of this disclosure is information associated with the effect of habituation program 140 on user's neurological behavior 128. For example, and without limitation, adaptability data 164 may include information indicating that the user's neurological behavior 128 has improved since the last iteration. In another non limiting example, adaptability data 164 may indicate that a habit has been formed or is in the process of being formed following adherence to habituation program 140. In one or more embodiments, adaptability data 164 may include information associated with physiological responses by the user based on the user's adherence to habituation program 140. For example, and without limitation, adaptability data 164 may include a physiological response such as a decrease in heart rate, an increase in blood oxygen levels, an increase or decrease in blood pressure and the like. In one or more embodiments, physiological responses may be compared to a previously recorded physiological response such as from a first iteration in which user interacted with system 100 and/or a previous iteration in which user interacted with system 100. In one or more embodiments, adaptability data 164 may include information associated with user's neurological behavior 128, such as but not limited to, increases in happiness, decrease in anxiety, increase in stress, information indicating formation of a habit, information indicating elimination of an addiction and the like.

With continued reference to FIG. 1, adaptability data 164 may include feedback data 156 as described above. In one or more embodiments, processor 108 may be configured to receive feedback data 156 from user following generation of habituation program 140 wherein feedback data 156 may be used for future habituation programs 140 and/or updated habituation programs 186 as described below. In one or more embodiments, processor 108 may first be configured to generate habituation program 140 and then receive feedback data 156 from user indicating the user's adaptability to habituation program 140. In one or more embodiments, feedback data 156 may be used to iteratively train habituation machine learning model 144. In one or more embodiments, feedback data 156 may include the user's adaptability to habituation program 140 such as but not limited to, adherence to the instructions of habituation program 140, recognized neurological changes due the user's adherence to habituation program 140, the user's happiness levels on the program, the user's anxiety levels, the user's weight, the user's lifestyle, the user's sleep patterns, the user's average heart rate, the user's religious level and the like. In one or more embodiments, adaptability data 164 and/or feedback data 156 may be received following generation of habituation program 140. In one or more embodiment, feedback data 156 may indicate user's likes or dislikes of habituation program 140. In one or more embodiments, habituation machine learning model 144 may be iteratively trained with feedback data 156 wherein future generation of habituation program 140 may generate outputs as a function of feedback received from adaptability data 164 or feedback data 156. In one or more embodiments, feedback data 156 may include information such as which steps or treatments were followed within habituation program 140, whether neurological behaviors 128 were modified due to adherence to habituation program 140 and the like.

With continued reference to FIG. 1, adaptability data 164 may include physiological responses. As described in this disclosure "physiological responses" refers to physical changes associated with a user's body. This may include but is not limited to, changes in heart rate, changes in blood oxygen levels, changes in blood pressure, changes in sleep patterns and the like. In one or more embodiments, a user's heart rate level may be associated with physiological responses, such as but not limited to, stress levels, physical exertion levels m emotional states and the like. In one or more embodiments, heart rates and/or any other adaptability data may be used to determine a user's stress levels, physical exertion levels and the like. In one or more embodiments, physiological responses may further include but are not limited to, any physiological or biological reactions, of a user's body such as but not limited to, stress levels, physical exertion levels, emotional states and the like. In one or more embodiments, adaptability data 164 may include information associated with physiological responses of the user following adherence of adaptability program. In one or more embodiments physiological responses may be received from sensors in contact with user. In one or more embodiments, sensors may include and/or be included within wearable device. In one or more embodiments, adaptability data 164 may include physiological responses that can be measured by sensor 136 and/or wearable device. In one or more embodiments, processor 108 may be configured to receive a current physiological response 168. A "current physiological response" for the purposes of this disclosure is information associated with physiological responses received for the current iteration of the processing. For example, and without limitation, current physiological response 168 may include information received for the purposes of determining user's adaptability to habituation program 140. In one or more embodiments, current physiological response 168 may include a neurological impact of user. A "Neurological impact" for the purposes of this disclosure is a change to a user's neurological functions. In one or more embodiments, neurological impact may include changes to user's brainwaves, changes to a user's neurological behavior 128, and/or any other changes affecting a user's brain or nervous system. In contrast, A "previous physiological response" for the purposes of this disclosure refers to physiological responses received for processing of previous iterations of system or prior to generation of habituation program 140. For example, and without limitation, previous physiological response 172 may include information received prior to habituation program 140 or on a previous, day month and the like. In one or more embodiments, previous physiological response 172 may be references as a base level wherein a user's adaptability to habituation program 140 may be determined by comparing current physiological responses 168 to previous physiological responses 172. In one or more embodiments, processor 108 may determine adaptability to habituation program 140 by comparing current physiological response 168 to previous physiological response 172. In one or more embodiments, previous physiological response 172 may be stored within user data 120 and/or on database 116. In one or more embodiments, previous physiological response 172 may be received on a previous day, month and the like. In one or more embodiments, changes between current physiological response 168 and previous physiological response 172 may indicate adaptability to habituation program 140. For example, and without limitation, an increase in sleep, a decrease in blood pressure, an increase in blood oxygen, an increase or decrease in heart rate may be indicative of changes in neurological behavior 128 and/or adaptability to habituation program 140.

With continued reference to FIG. 1, in a non-limiting embodiment, processor 108 may determine adaptability data 164 and/or adaptability to habituation program 140 by receiving heart rate data 176 from sensor 136 and/or wearable device. In one or more embodiments, processor 108 may determine current physiological response 168 as a function of heart rate data 176. "Heart rate data" for the purposes of this disclosure is information associated with user's heart rate. In one or more embodiments, heart rate data 176 may be tracked over a given period of time. In one or more embodiments, heart rate data 176 may indicate beats per minute at various times in the day. In one or more embodiments, heart rate data 176 may be received from one or more sensors such as wearable device. In one or more embodiments, current physiological response 168 may include heart rate data 176. In one or more embodiments, heart rate data 176 may be recorded following generation of habituation program 140 wherein heart rate data 176 may be used to determine adaptability to habituation program 140. In one or more embodiments, heart rate data 176 may be recorded for a timeframe of a month, two months and the like. In one or more embodiments, heart rate data 176 may be continuously received over a given period of time from when habituation program 140 has been generated until adaptability is determined.

With continued reference to FIG. 1, processor 108 may use heart rate data 176 to generate current physiological response 168. In one or more embodiments, processor 108 may determine current physiological response 168 using a physiological machine learning model 180. In one or more embodiments, physiological machine learning model 180 may be configured to receive heart rate data 176 and output current physiological response 168. In one or more embodiments, changes in heart variability and/or skin conductance levels may be associated with emotional and/or cognitive states which can reflect underlying brain activity. In one or more embodiments, physiological machine learning model 180 may be trained to correlated physiological data such as heart rate data 176 to neurological states. In one or more embodiments, embodiments, wearable device may receive information associated with physical activity, sleep patterns and/or any other activity that may be attributed to habit formation wherein trends within the information may indicate changes in habit formation. In one or more embodiments, changes in physical activity, changes in sleep and the like may indicate changes in neurological behavior 128. In one or more embodiments, heart rate variability received from sensor 136 and/or wearable device may be indicative of stress levels and emotional levels. In one or more embodiments, heart rate variability may be used to determine an impact on neurological behavior 128 such as habit formation. In one or more embodiments, a combination of heart rate data 176, accelerometers, gyroscopes and the like may be used to measure sleep activity, physical activity and the like. In one or more embodiments, location sensors may further be used to determine arability wherein the presence of a user at a particular location (e.g. gym, bar, club, park, etc.) may be indicative of changes to a user's neurological behavior 128. In one or more embodiments, processor 108 may receive physiological training data 184 including a plurality of heart rate data 176 correlated to a plurality of current physiological responses 168. In one or more embodiments, physiological machine learning model 180 may be generated as a function of phycological training data. In one or more embodiments, physiological machine learning model 180 may be configured to generate current physiological response 168 as a function of heart rate and physiological training data 184. In one or more embodiments, physiological training data 184 may be generated by a user, third party and the like. In one or more embodiments, physiological training data 184 may be iteratively trained by adjusting parameter values 152 similar to that of habituation machine learning model 144.

With continued reference to FIG. 1, processor 108 is configured to generate updated habituation program 186 as a function of user's adaptability to habituation program 140. An "Updated habituation program" for the purposes of this disclosure is a habituation program 140 that has been modified or changed in order to better suit the user in comparison to habituation program. For example, and without limitation, updated habituation program 186 may include new sets of instructions that replace sets of instructions within habituation program 140. In one or more embodiments, updated habituation program 186 may include new treatment generated based on user's adaptability, new steps based on user's adaptability and/or feedback and the like. In one or more embodiments, adaptability data 164 may be used as feedback data 156 to habituation machine learning model 144. In one or more embodiments, positive changes between current physiological response 168 and previous physiological response 172 may indicate positive feedback to habituation machine learning model 144. In one or more embodiments, negative changes between current physiological response 168 and previous physiological response 172 may indicate negative feedback wherein habituation machine learning model 144 may be configured to generate updated steps or instructions. In one or more embodiments, processor 108 may be configured to generate new treatment plans, and the like based on feedback data 156 and/or adaptability data 164. In one or more embodiments, adaptability data 164 may indicate that a particular set of steps or instructions were not beneficial and as a result, remove them. In one or more embodiments, adaptability data 164 and/or current physiological response 168 may indicate neurological impact wherein information associated with a positive neurological impact may be used to keep particular elements of habituation program 140 wherein information associated with a negative neurological impact may be used to remove or modify elements and or treatment within habituation program 140. In one or more embodiment, processor 108 may be configured to remove elements of habituation program 140 and/or configure habituation machine learning model 144 to generate alternate element of habituation program 140 as a function of adaptability data 164. In one or more embodiments, processor 108 may receive adaptability data 164 such as feedback data 156 and update habituation program 140. In one or more embodiments, generating the updated habituation program 186 as a function of the user's adaptability to the habituation program 140 includes generating the updated habituation program 186 as a function of the feedback data 156. In one or more embodiments, feedback data 156 may indicate treatments and/or instructions given to user in which user was not satisfied and/or did not adhere to wherein updated habituation program 186 may include habituation program 140 containing new treatments or instruction to replace the treatments or instruction in which user did not adhere to.

With continued reference to FIG. 1, updated habituation program 186 may include a neurological improvement. A "Neurological improvement" for the purposes of this disclosure is a positive change associated with a user's neurological behavior 128. For example, and without limitation, neurological improvement may include information indicating elevated sleep activity, decreased stress as indicated by heart rate data 176, decreased frequency in visiting unhealthy locations, improvements to a user's habits, improvements to addiction, improvements to religious levels and the like. In one or more embodiments neurological improvement may be generated using adaptability data 164 wherein positive changes indicated within adaptability data 164 may be used for neurological improvement. In one or more embodiments, neurological improvement may include positive changes in comparison to current physiological response 168 and previous physiological response 172.

With continued reference to FIG. 1, processor 108 may be configured to create a user interface data structure 188 as a function of at least updated habituation program 186. As used in this disclosure, "user interface data structure" is a data structure representing a specialized formatting of data on a computer configured such that the information can be effectively presented for a user interface. User interface data structure 188 may include any information as described in this disclosure, such as but not limited to updated habituation program 186, feedback data 156, and the like.

With continued reference to FIG. 1, processor 108 may be configured to transmit the user interface data structure 188 to a graphical user interface. Transmitting may include, and without limitation, transmitting using a wired or wireless connection, direct, or indirect, and between two or more components, circuits, devices, systems, and the like, which allows for reception and/or transmittance of data and/or signal(s) therebetween. Data and/or signals therebetween may include, without limitation, electrical, electromagnetic, magnetic, video, audio, radio, and microwave data and/or signals, combinations thereof, and the like, among others. Processor 108 may transmit the data described above to database 116 wherein the data may be accessed from database 116. Processor 108 may further transmit the data above to a device display 196 or another computing device 104.

With continued reference to FIG. 1, apparatus may include a graphical user interface (GUI 192). For the purposes of this disclosure, a "user interface" is a means by which a user and a computer system interact. For example, through the use of input devices and software. In some cases, processor 108 may be configured to modify graphical user interface as a function of at least updated habituation program 186 and visually present updated habituation program 186 through GUI 192. A user interface may include graphical user interface, command line interface (CLI), menu-driven user interface, touch user interface, voice user interface (VUI), form-based user interface, any combination thereof and the like. In some embodiments, a user may interact with the user interface using a computing device 104 distinct from and communicatively connected to processor 108. For example, a smart phone, smart tablet, or laptop operated by the user and/or participant. A user interface may include one or more graphical locator and/or cursor facilities allowing a user to interact with graphical models and/or combinations thereof, for instance using a touchscreen, touchpad, mouse, keyboard, and/or other manual data entry device. A "graphical user interface," as used herein, is a user interface that allows users to interact with electronic devices through visual representations. In some embodiments, GUI 192 may include icons, menus, other visual indicators, or representations (graphics), audio indicators such as primary notation, and display information and related user controls. A menu may contain a list of choices and may allow users to select one from them. A menu bar may be displayed horizontally across the screen such as pull-down menu. When any option is clicked in this menu, then the pull-down menu may appear. A menu may include a context menu that appears only when the user performs a specific action. An example of this is pressing the right mouse button. When this is done, a menu may appear under the cursor. Files, programs, web pages and the like may be represented using a small picture in graphical user interface. Persons skilled in the art, upon reviewing the entirety of this disclosure, will be aware of various ways in which a graphical user interface and/or elements thereof may be implemented and/or used as described in this disclosure.

With continued reference to FIG. 1, GUI 192 may contain one or more interactive elements. An "interactive element" for the purposes of this disclosure is an element within a graphical user interface that allows for communication with apparatus by a user. For example, and without limitation, interactive elements may include push buttons wherein selection of a push button, such as for example, by using a mouse, may indicate to system to perform a particular function and display the result through graphical user interface. In one or more embodiments, interactive element may include push buttons on GUI 192, wherein the selection of a particular push button may result in a particular function. In one or more embodiments, interactive elements may include words, phrases, illustrations and the like to indicate the particular process the user would like system to perform. In one or more embodiments, interaction with interactive elements may result in the display of updated habituation program 186. In one or more embodiments, GUI 192 may be configured to visualize differing portions of updated habituation program 186 such as differing treatments and/or steps within updated habituation program 186 wherein interactive element may be configured to allow for viewing of a particular portion of updated habituation program 186.

Referring now to FIG. 2, exemplary domains 200 are illustrated by way of a table. As can be seen domains may include vocational 204, marriage 208, family 212, health 216, virtue 220, emotional 224, financial 228, spiritual 232, intellectual 236, lifestyle 240, interest 244, and social 248 to name a few. Each domain 200 may have a status. Exemplary, non-limiting statuses include breakthrough, emerging, growth, plateau, stagnation, and depletion to name a few. In some cases, a domain status may be determined according to one or more state variables. State variable may be affected by objective data and/or subjective data. Exemplary non-limiting examples of objective data include medical measurements, time spent on certain activities, events participated in, number of steps taken, and generally speaking anything that can be measured. In some cases, remote device may directly measure or infer objective data, for example remote device may measure number of steps taken by group, amount of screen time, and the like. Alternatively or additionally objective data may be input by group into remote device. For example, a group may include group weight, group blood pressure, or any other objective datum by way of remote device. In some cases, group may input subjective data, for example by way of remote device. Subjective data may include a numerical representation (e.g., 1-10 rating) of how a group thinks or feels about a current aspect relating to a domain. For example a group may rate a level of anxiety, a level of fulfilment, or the like. In an embodiment, one or more domains may be selected and/or isolated by a group. This may allow for a more focused and concentrated experience on one or more domains of interest to a group. In an embodiment, a group may select one or more domains to isolate and/or focus on. In yet another non-limiting example, computing device 104 may select one or more domains for a group to focus on, using a selection process that may include one or more machine learning processes as described throughout this application.

With continued reference to FIG. 2, at least a domain may include vocational domain 204. Objective data that may be associated with vocational domain includes title, role, responsibility, compensation, and the like. Subjective data may include a rating of group's level of vocational fulfilment. A domain target associated with vocational domain 204 may include a change in a subjective or objective datum associated with the vocational domain 204. Schedule components or events that may be added to exploit value in vocational domain 204 include professional training events, maximizing contribution, exploiting opportunities, and the like.

With continued reference to FIG. 2, at least a domain may include marriage domain 208. Objective data that may be associated with marriage domain includes amount of time spent with spouse, for example time spent enjoying one another. Subjective data may include a rating of group's level of marriage fulfilment. A domain target associated with marriage domain 208 may include a change in a subjective or objective datum associated with the marriage domain 208. Schedule components or events that may be added to exploit value in marriage domain 208 include events determined to maximize marriage fulfilment, including participating in couple centric events, self-sacrificial acts of love, couples therapy, honest communication sessions, and the like.

With continued reference to FIG. 2, at least a domain may include family domain 212. Objective data that may be associated with family domain includes amount of time spent with family. Subjective data may include a rating of group's level of family fulfilment or a rating of a family member's level of fulfilment with group/spouse. A domain target associated with family domain 212 may include a change in a subjective or objective datum associated with the family domain 212. Schedule components or events that may be added to exploit value in family domain 212 include events determined to maximize family fulfilment, including participating in family events, self-sacrificing acts of love, generosity of time, money, and service, and the like.

With continued reference to FIG. 2, at least a domain may include health domain 216. Objective data that may be associated with health domain includes medical data, such as without limitation body mass index, blood pressure, resting heart rate, blood oxygen content, and the like. Subjective data may include a rating of group's level of health fulfilment, a rating of number of activities a group feels are impaired by health concerns, a rating of overall concern with health, and the like. A domain target associated with health domain 216 may include a change in a subjective or objective datum associated with the health domain 216. Schedule components or events that may be added to exploit value in health domain 216 include events determined to maximize health fulfilment, exercise, nutritional meals, visits to medical professionals, and the like.

With continued reference to FIG. 2, at least a domain may include virtue domain 220. Objective data that may be associated with virtue domain includes amount of time acting virtuously, proportion of big decisions which are aligned with desirable virtues, amount of success or failure living within targeted virtue levels, evidence of retained or unretained resolve, and the like. Subjective data may include a rating of group's self-perceived level of virtue or a rating of group's perceived level of virtue from another. A domain target associated with virtue domain 220 may include a change in a subjective or objective datum associated with the virtue domain 220. Schedule components or events that may be added to exploit value in virtue domain 220 include events determined to maximize virtue fulfilment, including participating habit building exercises designed to facilitate consistently good decision making.

With continued reference to FIG. 2, at least a domain may include emotional domain 224. Objective data that may be associated with emotional domain includes amount of time spent in a state of emotional destress, amount of time in emotional harmony, amount of time sleeping, caloric intake, amount of time engaged in anxiety about the past or imagined future, and the like. Subjective data may include a rating of group's level of emotional fulfilment. A domain target associated with emotional domain 224 may include a change in a subjective or objective datum associated with the emotional domain 224. Schedule components or events that may be added to exploit value in emotional domain 224 include therapy, treatment under the supervision of health care professionals, events and exercises that are likely to improve a group's emotions, and the like.

With continued reference to FIG. 2, at least a domain may include financial domain 228. Objective data that may be associated with financial domain includes amount of financial assets possessed by group. Subjective data may include a rating of group's sense of financial security independence and freedom. A domain target associated with financial domain 228 may include a change in a subjective or objective datum associated with the financial domain 228. Schedule components or events that may be added to exploit value in financial domain 228 include meeting with a financial advisor, increasing savings contributions, budgeting, and the like.

With continued reference to FIG. 2, at least a domain may include intellectual domain 236. Objective data that may be associated with intellectual domain includes amount performance in intellectual pursuits, such as graded performance in school. Subjective data may include a rating of group's level of intellectual fulfilment. A domain target associated with intellectual domain 236 may include a change in a subjective or objective datum associated with the intellectual domain 236. Schedule components or events that may be added to exploit value in intellectual domain 236 include events determined to maximize intellectual fulfilment, including enrolling in educational programs, enjoying cultural events, and the like.

With continued reference to FIG. 2, at least a domain may include lifestyle domain 240. Objective data that may be associated with lifestyle domain includes amount of time spent in ideal or unideal lifestyle settings. Subjective data may include a rating of group's level of lifestyle fulfilment. A domain target associated with lifestyle domain 240 may include a change in a subjective or objective datum associated with the lifestyle domain 240. Schedule components or events that may be added to exploit value in lifestyle domain 240 include events determined to maximize lifestyle fulfilment, including housing, travel, wardrobe, toys, activities, groups and free time.

With continued reference to FIG. 2, at least a domain may include interest domain 244. Objective data that may be associated with interest domain includes amount of time on avocational pursuits or personally enjoyable activities. Subjective data may include a rating of group's level of interest fulfilment. A domain target associated with interest domain 244 may include a change in a subjective or objective datum associated with the interest domain 244. Schedule components or events that may be added to exploit value in interest domain 244 include events determined to maximize interest fulfilment, including hobbyist events, and the like.

With continued reference to FIG. 2, at least a domain may include social domain 248. Objective data that may be associated with social domain includes amount of time spent with others in a social setting, for example time spent enjoying one another. Subjective data may include a rating of group's level of social fulfilment. A domain target associated with social domain 248 may include a change in a subjective or objective datum associated with the social domain 248. Schedule components or events that may be added to exploit value in social domain 248 include events determined to maximize social fulfilment, including participating in social events, engaging with a club, friends, groups, entertainment events, and the like.

Figure 3:
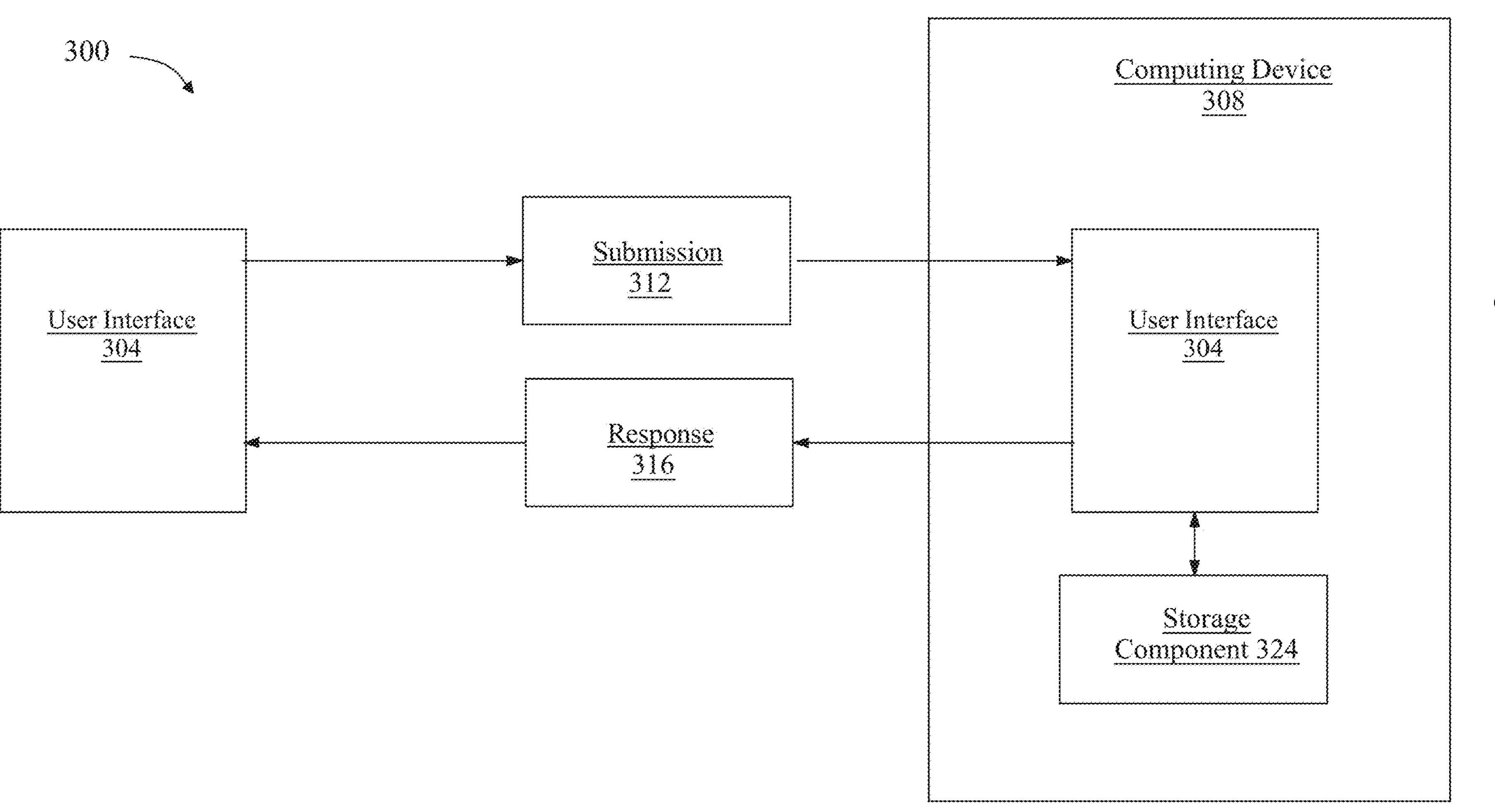
FIG. 3 illustrates is an exemplary embodiment of a chatbot system.

Referring to FIG. 3, a chatbot system 300 is schematically illustrated. According to some embodiments, a user interface 304 may be communicative with a computing device 308 that is configured to operate a chatbot. In some cases, user interface 304 may be local to computing device 308. Alternatively or additionally, in some cases, user interface 304 may remote to computing device 308 and communicative with the computing device 308, by way of one or more networks, such as without limitation the internet. Alternatively or additionally, user interface 304 may communicate with a user device and/or computing device 308 using telephonic devices and networks, such as without limitation fax machines, short message service (SMS), or multimedia message service (MMS). Commonly, user interface 304 communicates with computing device 308 using text-based communication, for example without limitation using a character encoding protocol, such as American Standard for Information Interchange (ASCII). Typically, a user interface 304 conversationally interfaces a chatbot, by way of at least a submission 312, from the user interface 304 to the chatbot, and a response 316, from the chatbot to the user interface 304. In many cases, one or both submission 312 and response 316 are text-based communication. Alternatively or additionally, in some cases, one or both of submission 312 and response 316 are audio-based communication.

Continuing in reference to FIG. 3, a submission 312 once received by computing device 308 operating a chatbot, may be processed by a processor. In some embodiments, processor processes a submission 312 using one or more keyword recognition, pattern matching, and natural language processing. In some embodiments, processor employs real-time learning with evolutionary algorithms. In some cases, processor may retrieve a pre-prepared response from at least a storage component 324, based upon submission 312. Alternatively or additionally, in some embodiments, processor communicates a response 316 without first receiving a submission 312, thereby initiating conversation. In some cases, processor communicates an inquiry to user interface; and the processor is configured to process an answer to the inquiry in a following submission 312 from the user interface. In some cases, an answer to an inquiry present within a submission 312 from a user device may be used by computing device 104 as an input to another function.

Figure 4:
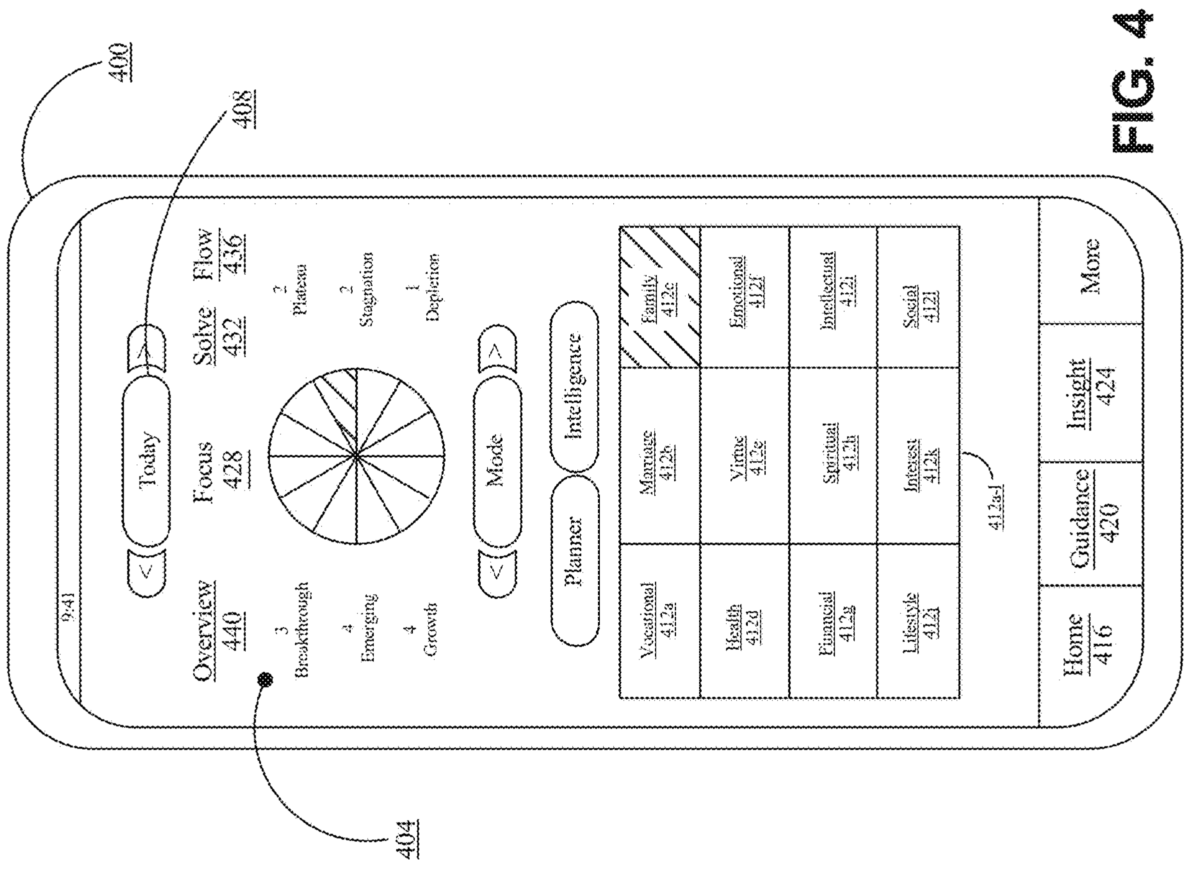
FIG. 4 is an exemplary remote device including an exemplary graphical user interface of a remote device.

Referring now to FIG. 4, an exemplary embodiment of a remote device 400 is illustrated. In some cases, remote device 400 may interface with user by way of a graphical user interface (GUI) 404. In some cases, remote device 400 may display to user a schedule 408, such as without limitation a weekly schedule. In some cases, schedule 408 function allows a user to view and edit a user schedule. In some embodiments, schedule 408 may be an optimal user schedule generated using a computing device, such as, for example, optimal user schedule and computing device 104 discussed with reference to FIG. 1. In some cases, remote device 400 may display to user domains 412*a*-1. In some cases, progress (e.g., evaluation results) related to a domain may be represented by GUI, such as by way of color coding. For example, family domain 412*c* is indicated with hashmarks to indicate that family is an undesirable (e.g., depleted) status. In some cases, a status for each domain may be indicated to user by way of GUI 404, for example in an "view 416. In some cases, GUI may allow user access to resources. In some cases, resources may be domain specific. Exemplary resources include guidance 420 and insight 424. Guidance 420 may include any audio information designed to enrich a user, for example within a specific domain. Insight 424 may include any media, such as video, text, and the like intended to enrich a user, for example within a specific domain. Focus 428 may isolate one or more domains that may aid in a more focused and concentrated experience to assist in driving change and progress. Solve 432 may include a scheduled focus for a particular period of time such as a day, week, month, quarter, year, and the like. Solve 432 may display information pertaining to particular issues and problems to solve and may aid in selecting one or more breakthrough domains. Flow 436 may include habits, projects, rocks and to-dos that may be aligned with a user's priorities and interests. Overview 440 may include a big picture view of domains, realms, and/or categories. Notebook 444 and/or intelligence 448 may include one or more digital copies of handwritten tools that may be integrated and automatically updated and available within graphical user interface 404.

In some embodiments, GUI 404 may enable a user to interact with specific resources of a domain. For example, when a user interacts with home 416, GUI 404 may illuminate domains 412*a*-1 with different colors based at least on a status of each domain. Additionally, one or more domains may be considered as an undesirable status (e.g., depleted). As described in the above example, FIG. 4 illustrates family domain 412*c* being depleted. In some embodiments, display box for family domain 412*c* may be pulsating. That is, display box for family domain 412*c* may appear to rise and fall into the plane of GUI 404. This may draw a user's attention to family domain 412*c*. The pulsating feature may be especially beneficial for users with sight problems such as color blindness. In some embodiments, display box for family domain 412*c* may be interacted with and maximized to a full screen mode. While in full screen, a plurality of lessons and their respective completion statuses may be displayed. It should be noted that the full screen capability may be available upon interacting with any domain display box and is not limited to undesirable status domains. In some embodiments, full screen mode may be an automatic response to a user interacting with home 416. For example, a user may interact with home 416 and in response to the user's interaction, a full screen mode of one or more undesirable status domains, with their respective plurality of lessons and completion statuses, will be displayed.

Figure 5:
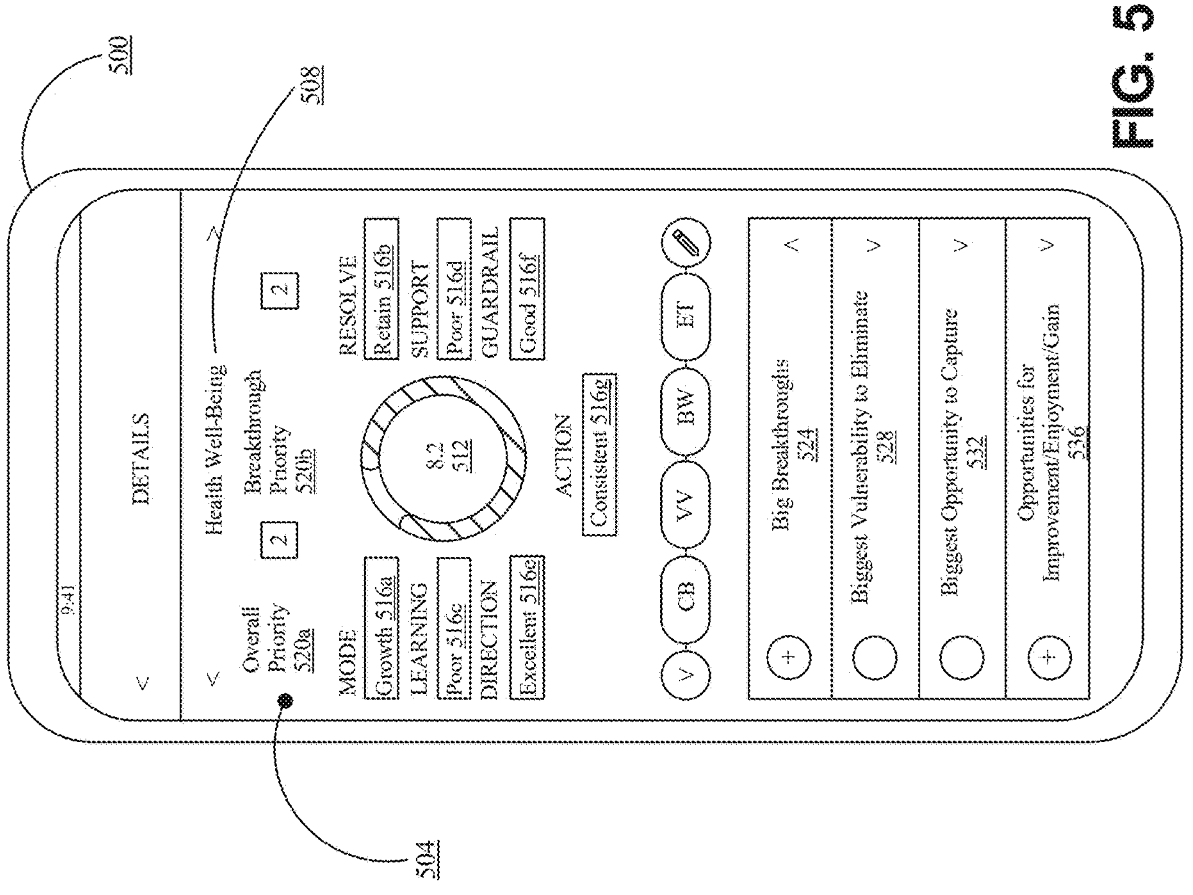
FIG. 5 is an exemplary remote device including an exemplary graphical user interface of a remote device.

Referring now to FIG. 5, an exemplary remote device 500 is illustrated. In some cases, remote device 500 may interface with group by way of a graphical group interface (GUI) 504. In some cases, remote device 500 may display domain-specific information 508, for instance information related to health domain. In some cases, an overall domain-specific rating 512 (i.e., evaluation result) may be presented to group. Additionally, subordinate domain-specific ratings (i.e., evaluation results) 516*a*-*g* may be presented to group. For example, subordinate domain-specific ratings may be related to mode 516*a*, resolve 516*b*, learning 516*c*, support 516*d*, direction 516*e*, guardrail 516*f*, action 516*g*, and the like. In some cases, a domain may be prioritize, for example with an overall priority 520*a* and/or a breakthrough priority 520*b*. In some cases, domain-specific information may be enumerated and/or prioritized. Exemplary enumerations and/or prioritizations include without limitation big breakthroughs 524, biggest vulnerability to eliminate 528, biggest opportunity to capture 532, opportunities for improvement/enjoyment/gain 536, and the like.

Figure 6:
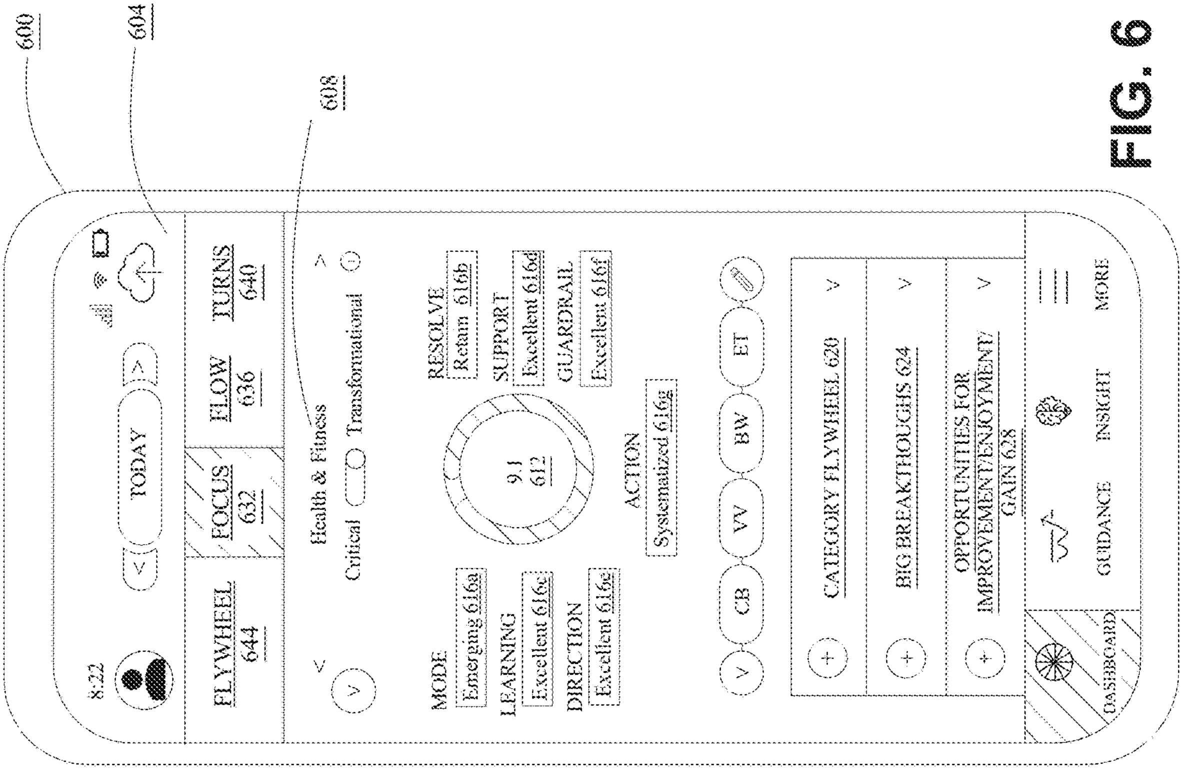
FIG. 6 is an exemplary remote device including an exemplary graphical user interface of a remote device illustrating the focus tab of the dashboard screen of a user with an excellent performance level on a given day.

Referring now to FIG. 6, an exemplary remote device 600 including an exemplary graphical user interface 604 of a remote device illustrating the focus tab of the dashboard screen of a user with an excellent performance level on a given day. In some cases, remote device 600 may interface with system by way of a graphical user interface (GUI) 604. In some cases, remote device 600 may display domain-specific information 608, for instance information related to the health and fitness domain. In some cases, an overall domain-specific rating 612 (i.e., evaluation result) may be presented to system. Additionally, subordinate domain-specific ratings (i.e., evaluation results) 616*a-g* may be presented to system. For example, subordinate domain-specific ratings may be related to mode 616*a*, resolve 616*b*, learning 616*c*, support 616*d*, direction 616*e*, guardrail 616*f*, action 616*g*, and the like. In some cases, domain-specific information may be enumerated and/or prioritized. Exemplary enumerations and/or prioritizations include without limitation category flywheel 620, big breakthroughs 624, opportunities for improvement/enjoyment/gain 628, and the like. In some cases, focus 632 may isolate one or more domains that may aid in a more focused and concentrated experience to assist in driving change and progress. In some cases, flow 636 may include habits, projects, rocks and to-dos that may be aligned with a user's priorities and interests. In some cases, turns 640 may include information related to key turns over different time periods. In some cases, flywheel 644 may include a big picture view of domains, realms, and/or categories.

Figure 7:
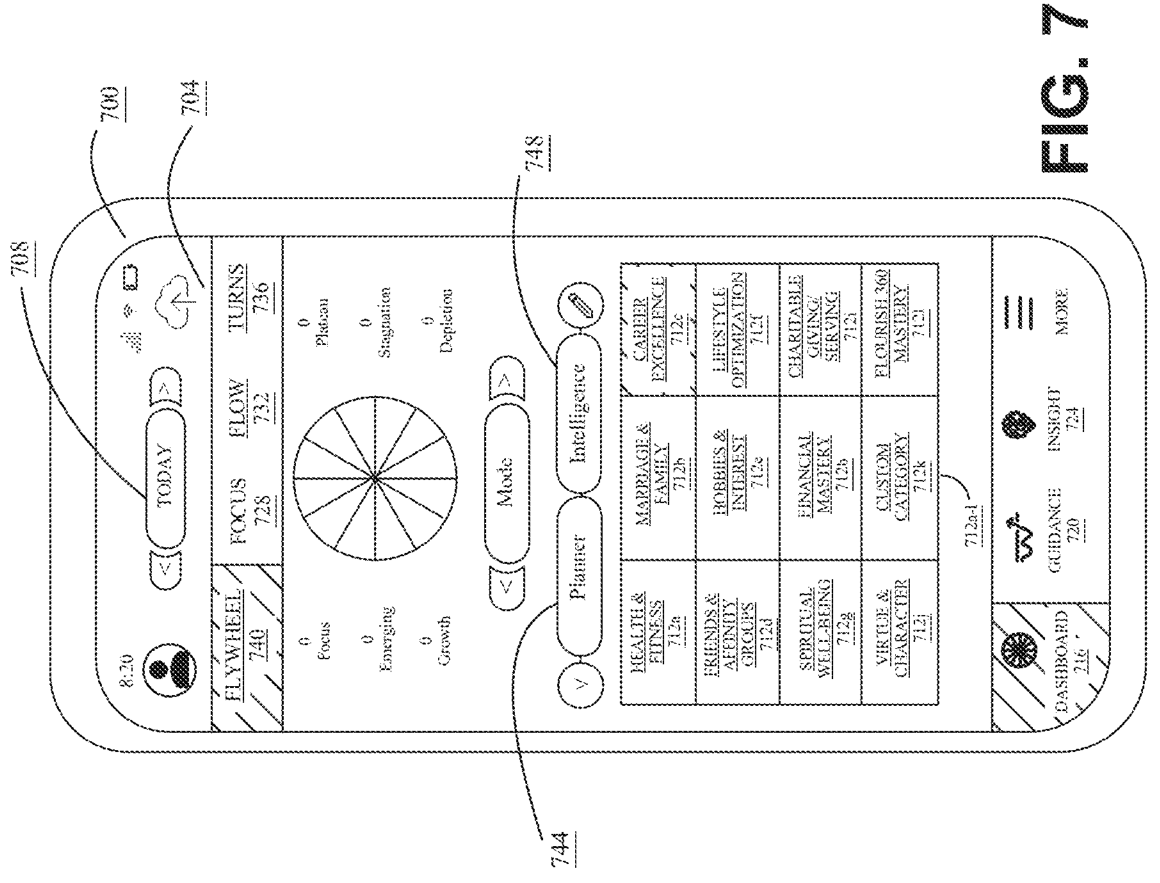
FIG. 7 is an exemplary remote device including an exemplary graphical user interface of a remote device illustrating the flywheel tab of the dashboard screen with exemplary domains.

Referring now to FIG. 7, an exemplary remote device 700 including an exemplary graphical user interface 704 of a remote device illustrating the flywheel tab of the dashboard screen with exemplary domains. In some cases, remote device 700 may interface with user by way of a graphical user interface (GUI) 704. In some cases, remote device 700 may display to user a schedule 708, such as without limitation a weekly schedule. In some cases, schedule 708 function allows a user to view and edit a user schedule. In some embodiments, schedule 708 may be an optimal user schedule generated using a computing device. In some cases, remote device 700 may display to user domains 712*a*-1. In some cases, progress (e.g., evaluation results) related to a domain may be represented by GUI, such as by way of color coding. For example, career excellence domain 712*c* is indicated with hashmarks to indicate that career excellence is an undesirable (e.g., depleted) status. In some cases, a status for each domain may be indicated to user by way of GUI 704, for example in dashboard 716. In some cases, GUI may allow user access to resources. In some cases, resources may be domain specific. Exemplary resources include guidance 720 and insight 724. Guidance 720 may include any audio information designed to enrich a user, for example within a specific domain. Insight 724 may include any media, such as video, text, and the like intended to enrich a user, for example within a specific domain. Focus 728 may isolate one or more domains that may aid in a more focused and concentrated experience to assist in driving change and progress. Flow 732 may include habits, projects, rocks and to-dos that may be aligned with a user's priorities and interests. Turns 736 may include information related to key turns over different time periods. Flywheel 740 may include a big picture view of domains, realms, and/or categories. Planner 744 and/or intelligence 748 may include one or more digital copies of handwritten tools that may be integrated and automatically updated and available within graphical user interface 704.

In some embodiments, GUI 704 may enable a user to interact with specific resources of a domain. For example, when a user interacts with dashboard 716, GUI 704 may illuminate domains 712*a*-1 with different colors based at least on a status of each domain. Additionally, one or more domains may be considered as an undesirable status (e.g., depleted). As a non-limiting example, FIG. 7 illustrates marriage & family domain 712*b* being depleted. In some embodiments, display box for career excellence 712*c* may be pulsating. That is, display box for career excellence 712*c* may appear to rise and fall into the plane of GUI 704. This may draw a user's attention to career excellence 712*c*. The pulsating feature may be especially beneficial for users with sight problems such as color blindness. In some embodiments, display box for career excellence domain 712*c* may be interacted with and maximized to a full screen mode. While in full screen, a plurality of lessons and their respective completion statuses may be displayed. It should be noted that the full screen capability may be available upon interacting with any domain display box and is not limited to undesirable status domains. In some embodiments, full screen mode may be an automatic response to a user interacting with dashboard 716. For example, a user may interact with dashboard 716 and in response to the user's interaction, a full screen mode of one or more undesirable status domains, with their respective plurality of lessons and completion statuses, will be displayed.

Figure 8:
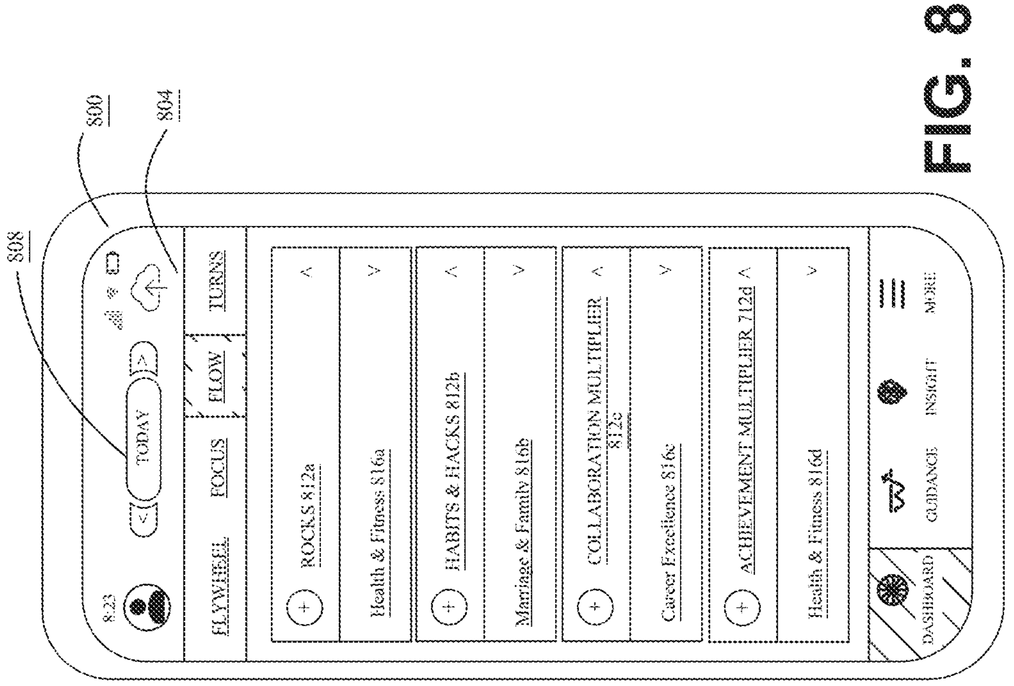
FIG. 8 is an exemplary remote device including an exemplary graphical user interface of a remote device.

Referring now to FIG. 8, an exemplary remote device 800 including an exemplary graphical user interface 804 of a remote device. In some cases, remote device 800 may interface with user by way of a graphical user interface (GUI) 804. In some cases, remote device 800 may display to user a schedule 808, such as without limitation a weekly schedule. In some cases, schedule 808 function allows a user to view and edit a user schedule. In some embodiments, schedule 808 may be an optimal user schedule generated using a computing device.

With continued reference to FIG. 8, remote device 800 may display suggestions 812*a-d* such as "Rocks" 812*a*, "Habits & Hacks" 812*b*, "Collaboration Multiplier" 812*c*, "Achievement Multiplier" 812*d*, and the like. Each suggestion category may include at least a domain with a respective drop-down menu option 816*a-d*. In some instances, at least a domain may be color coded to indicate a domain-specific rating. As a non-limiting example, at least a domain may be a green shade if a respective domain-specific rating is above a certain threshold (e.g., 8.1). Further, at least a domain may be a yellow shade if a respective domain-specific rating is below a certain threshold (e.g., 7.0). In some cases, at least a domain drop-down menu 816*a-d* may include one or more recommendations and/or one or more suggestions associated with the suggestion category and the at least a domain. As a non-limiting example, a drop-down option for "Habits & Hacks" 812*b* may include "Marriage & Family" 816*b* which may include habits and/or productivity hacks to improve a user's marriage and family relationships. Continuing the non-limiting example, "Habits & Hacks" 812*b* that improve the user's marriage and family relationships may include date night suggestions, suggested modification to hours, prioritizing the user's work tasks based on predetermined importance, and the like.

Figure 9:
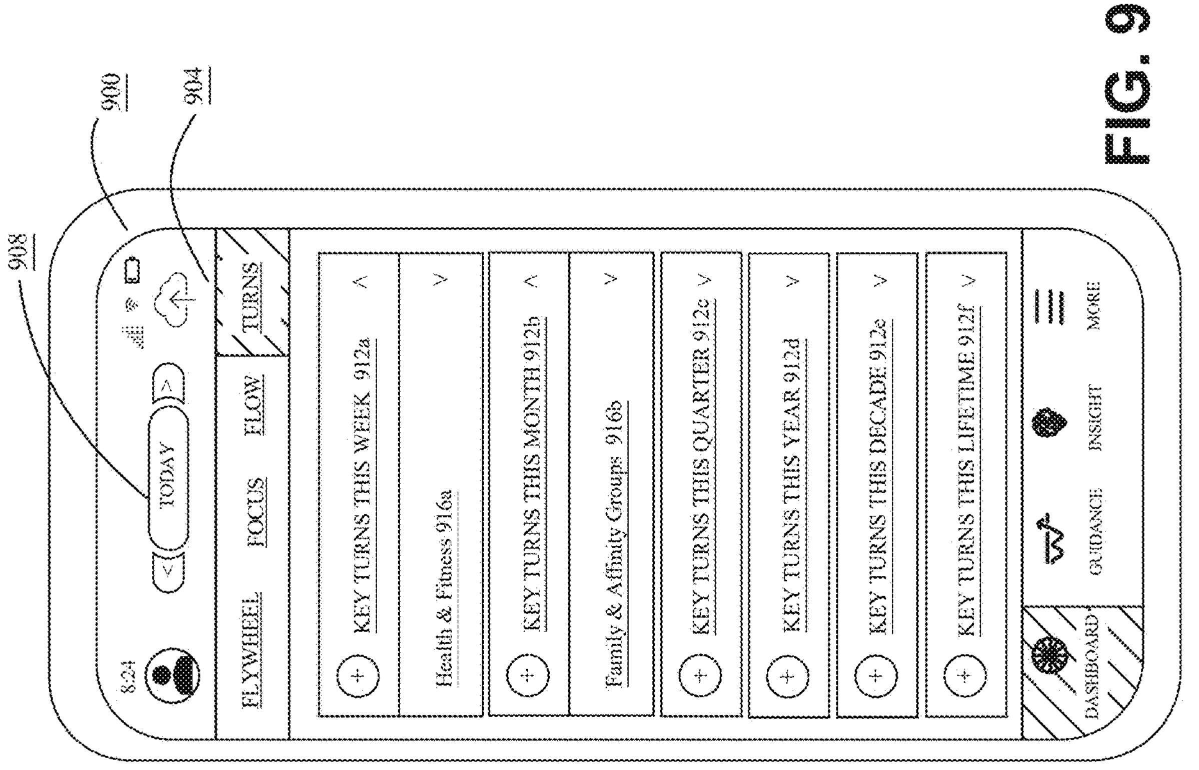
FIG. 9 is an exemplary remote device including an exemplary graphical user interface of a remote device.

Referring now to FIG. 9, an exemplary remote device 900 including an exemplary graphical user interface 904 of a remote device. In some cases, remote device 900 may interface with user by way of a graphical user interface (GUI) 904. In some cases, remote device 900 may display to user a schedule 908, such as without limitation a weekly schedule. In some cases, schedule 908 function allows a user to view and edit a user schedule. In some embodiments, schedule 908 may be an optimal user schedule generated using a computing device. In some cases, remote device 900 may display key turns 912*a-d* such as "Key Turns This Week" 912*a*, "Key Turns This Month" 912*b*, "Key Turns This Quarter" 912*c*, "Key Turns This Year" 912*d*, "Key Turns This Decade" 912*e*, "Key Turns This Lifetime" 912*f*, and the like. Each suggestion category may include at least a domain with a respective drop-down menu option 916*a-b*. In some instances, at least a domain may be color coded to indicate a domain-specific rating. As a non-limiting example, at least a domain may be a green shade if a respective domain-specific rating is above a certain threshold (e.g., 7.1). Further, at least a domain may be a yellow shade if a respective domain-specific rating is below a certain threshold (e.g., 7.0). In some cases, at least a domain drop-down menu 916*a-b* may include one or more recommendations and/or one or more suggestions associated with the suggestion category and the at least a domain. As a non-limiting example, a drop-down option for "Key Turns This Week" 912*a* may include "Health & Fitness" 916*a* which may include key turns regarding the upcoming week to improve a user's health and fitness goals.

Figure 10:
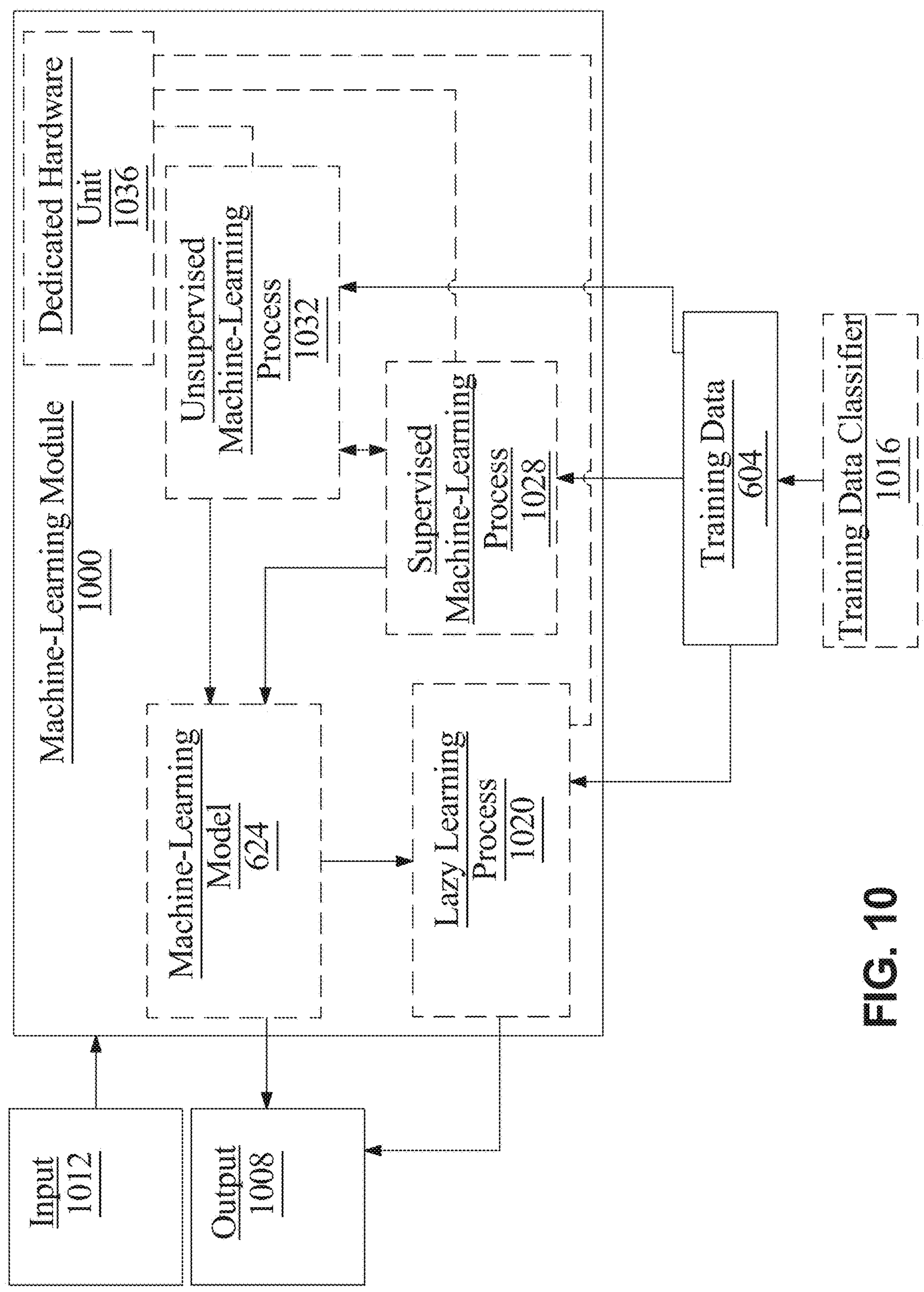
FIG. 10 is a block diagram of an exemplary machine-learning process.

Referring now to FIG. 10, an exemplary embodiment of a machine-learning module 1000 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that automatedly uses training data 1004 to generate an algorithm instantiated in hardware or software logic, data structures, and/or functions that will be performed by a computing device/module to produce outputs 1008 given data provided as inputs 1012; this is in contrast to a non-machine learning software program where the commands to be executed are determined in advance by a user and written in a programming language.

Still referring to FIG. 10, "training data," as used herein, is data containing correlations that a machine-learning process may use to model relationships between two or more categories of data elements. For instance, and without limitation, training data 1004 may include a plurality of data entries, also known as "training examples," each entry representing a set of data elements that were recorded, received, and/or generated together; data elements may be correlated by shared existence in a given data entry, by proximity in a given data entry, or the like. Multiple data entries in training data 1004 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 1004 according to various correlations; correlations may indicate causative and/or predictive links between categories of data elements, which may be modeled as relationships such as mathematical relationships by machine-learning processes as described in further detail below. Training data 1004 may be formatted and/or organized by categories of data elements, for instance by associating data elements with one or more descriptors corresponding to categories of data elements. As a non-limiting example, training data 1004 may include data entered in standardized forms by persons or processes, such that entry of a given data element in a given field in a form may be mapped to one or more descriptors of categories. Elements in training data 1004 may be linked to descriptors of categories by tags, tokens, or other data elements; for instance, and without limitation, training data 1004 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 10, training data 1004 may include one or more elements that are not categorized; that is, training data 1004 may not be formatted or contain descriptors for some elements of data. Machine-learning algorithms and/or other processes may sort training data 1004 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 1004 to be made applicable for two or more distinct machine-learning algorithms as described in further detail below. Training data 1004 used by machine-learning module 1000 may correlate any input data as described in this disclosure to any output data as described in this disclosure. As a non-limiting illustrative example inputs may include inputs such as user data, feedback data and/or adaptability data and outputs include outputs such as habituation program and/or updated habituation program.

Further referring to FIG. 10, training data may be filtered, sorted, and/or selected using one or more supervised and/or unsupervised machine-learning processes and/or models as described in further detail below; such models may include without limitation a training data classifier 1016. Training data classifier 1016 may include a "classifier," which as used in this disclosure is a machine-learning model as defined below, such as a data structure representing and/or using a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. A distance metric may include any norm, such as, without limitation, a Pythagorean norm. Machine-learning module 1000 may generate a classifier using a classification algorithm, defined as a processes whereby a computing device and/or any module and/or component operating thereon derives a classifier from training data 1004. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 1016 may classify elements of training data to neurological classes. In an embodiments, user data may be classified to a neurological class wherein the neurological class may indicate the particular type of neurological behavior.

Still referring to FIG. 10, computing device may be configured to generate a classifier using a Naïve Bayes classification algorithm. Naïve Bayes classification algorithm generates classifiers by assigning class labels to problem instances, represented as vectors of element values. Class labels are drawn from a finite set. Naïve Bayes classification algorithm may include generating a family of algorithms that assume that the value of a particular element is independent of the value of any other element, given a class variable. Naïve Bayes classification algorithm may be based on Bayes Theorem expressed as P(A/B)=P(B/A) P(A)=P(B), where P(A/B) is the probability of hypothesis A given data B also known as posterior probability; P(B/A) is the probability of data B given that the hypothesis A was true; P(A) is the probability of hypothesis A being true regardless of data also known as prior probability of A; and P(B) is the probability of the data regardless of the hypothesis. A naïve Bayes algorithm may be generated by first transforming training data into a frequency table. Computing device may then calculate a likelihood table by calculating probabilities of different data entries and classification labels. Computing device may utilize a naïve Bayes equation to calculate a posterior probability for each class. A class containing the highest posterior probability is the outcome of prediction. Naïve Bayes classification algorithm may include a gaussian model that follows a normal distribution. Naïve Bayes classification algorithm may include a multinomial model that is used for discrete counts. Naïve Bayes classification algorithm may include a Bernoulli model that may be utilized when vectors are binary.

With continued reference to FIG. 10, computing device may be configured to generate a classifier using a K-nearest neighbors (KNN) algorithm. A "K-nearest neighbors algorithm" as used in this disclosure, includes a classification method that utilizes feature similarity to analyze how closely out-of-sample-features resemble training data to classify input data to one or more clusters and/or categories of features as represented in training data; this may be performed by representing both training data and input data in vector forms, and using one or more measures of vector similarity to identify classifications within training data, and to determine a classification of input data. K-nearest neighbors algorithm may include specifying a K-value, or a number directing the classifier to select the k most similar entries training data to a given sample, determining the most common classifier of the entries in the database, and classifying the known sample; this may be performed recursively and/or iteratively to generate a classifier that may be used to classify input data as further samples. For instance, an initial set of samples may be performed to cover an initial heuristic and/or "first guess" at an output and/or relationship, which may be seeded, without limitation, using expert input received according to any process as described herein. As a non-limiting example, an initial heuristic may include a ranking of associations between inputs and elements of training data. Heuristic may include selecting some number of highest-ranking associations and/or training data elements.

With continued reference to FIG. 10, generating k-nearest neighbors algorithm may generate a first vector output containing a data entry cluster, generating a second vector output containing an input data, and calculate the distance between the first vector output and the second vector output using any suitable norm such as cosine similarity, Euclidean distance measurement, or the like. Each vector output may be represented, without limitation, as an n-tuple of values, where n is at least two values. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute/as derived using a Pythagorean norm:

$$l = \sqrt{\sum_{i=0}^{n} a_i^n},$$

where $a_i$ is attribute number i of the vector. Scaling and/or normalization may function to make vector comparison independent of absolute quantities of attributes, while preserving any dependency on similarity of attributes; this may, for instance, be advantageous where cases represented in training data are represented by different quantities of samples, which may result in proportionally equivalent vectors with divergent values.

With further reference to FIG. 10, training examples for use as training data may be selected from a population of potential examples according to cohorts relevant to an analytical problem to be solved, a classification task, or the like. Alternatively or additionally, training data may be selected to span a set of likely circumstances or inputs for a machine-learning model and/or process to encounter when deployed. For instance, and without limitation, for each category of input data to a machine-learning process or model that may exist in a range of values in a population of phenomena such as images, user data, process data, physical data, or the like, a computing device, processor, and/or machine-learning model may select training examples representing each possible value on such a range and/or a representative sample of values on such a range. Selection of a representative sample may include selection of training examples in proportions matching a statistically determined and/or predicted distribution of such values according to relative frequency, such that, for instance, values encountered more frequently in a population of data so analyzed are represented by more training examples than values that are encountered less frequently. Alternatively or additionally, a set of training examples may be compared to a collection of representative values in a database and/or presented to a user, so that a process can detect, automatically or via user input, one or more values that are not included in the set of training examples. Computing device, processor, and/or module may automatically generate a missing training example; this may be done by receiving and/or retrieving a missing input and/or output value and correlating the missing input and/or output value with a corresponding output and/or input value collocated in a data record with the retrieved value, provided by a user and/or other device, or the like.

Continuing to refer to FIG. 10, computer, processor, and/or module may be configured to preprocess training data. "Preprocessing" training data, as used in this disclosure, is transforming training data from raw form to a format that can be used for training a machine learning model. Preprocessing may include sanitizing, feature selection, feature scaling, data augmentation and the like.

Still referring to FIG. 10, computer, processor, and/or module may be configured to sanitize training data. "Sanitizing" training data, as used in this disclosure, is a process whereby training examples are removed that interfere with convergence of a machine-learning model and/or process to a useful result. For instance, and without limitation, a training example may include an input and/or output value that is an outlier from typically encountered values, such that a machine-learning algorithm using the training example will be adapted to an unlikely amount as an input and/or output; a value that is more than a threshold number of standard deviations away from an average, mean, or expected value, for instance, may be eliminated. Alternatively or additionally, one or more training examples may be identified as having poor quality data, where "poor quality" is defined as having a signal to noise ratio below a threshold value. Sanitizing may include steps such as removing duplicative or otherwise redundant data, interpolating missing data, correcting data errors, standardizing data, identifying outliers, and the like. In a nonlimiting example, sanitization may include utilizing algorithms for identifying duplicate entries or spell-check algorithms.

As a non-limiting example, and with further reference to FIG. 10, images used to train an image classifier or other machine-learning model and/or process that takes images as inputs or generates images as outputs may be rejected if image quality is below a threshold value. For instance, and without limitation, computing device, processor, and/or module may perform blur detection, and eliminate one or more Blur detection may be performed, as a non-limiting example, by taking Fourier transform, or an approximation such as a Fast Fourier Transform (FFT) of the image and analyzing a distribution of low and high frequencies in the resulting frequency-domain depiction of the image; numbers of high-frequency values below a threshold level may indicate blurriness. As a further non-limiting example, detection of blurriness may be performed by convolving an image, a channel of an image, or the like with a Laplacian kernel; this may generate a numerical score reflecting a number of rapid changes in intensity shown in the image, such that a high score indicates clarity and a low score indicates blurriness. Blurriness detection may be performed using a gradient-based operator, which measures operators based on the gradient or first derivative of an image, based on the hypothesis that rapid changes indicate sharp edges in the image, and thus are indicative of a lower degree of blurriness. Blur detection may be performed using Wavelet-based operator, which takes advantage of the capability of coefficients of the discrete wavelet transform to describe the frequency and spatial content of images. Blur detection may be performed using statistics-based operators take advantage of several image statistics as texture descriptors in order to compute a focus level. Blur detection may be performed by using discrete cosine transform (DCT) coefficients in order to compute a focus level of an image from its frequency content.

Continuing to refer to FIG. 10, computing device, processor, and/or module may be configured to precondition one or more training examples. For instance, and without limitation, where a machine learning model and/or process has one or more inputs and/or outputs requiring, transmitting, or receiving a certain number of bits, samples, or other units of data, one or more training examples' elements to be used as or compared to inputs and/or outputs may be modified to have such a number of units of data. For instance, a computing device, processor, and/or module may convert a smaller number of units, such as in a low pixel count image, into a desired number of units, for instance by upsampling and interpolating. As a non-limiting example, a low pixel count image may have 100 pixels, however a desired number of pixels may be 128. Processor may interpolate the low pixel count image to convert the 100 pixels into 128 pixels. It should also be noted that one of ordinary skill in the art, upon reading this disclosure, would know the various methods to interpolate a smaller number of data units such as samples, pixels, bits, or the like to a desired number of such units. In some instances, a set of interpolation rules may be trained by sets of highly detailed inputs and/or outputs and corresponding inputs and/or outputs downsampled to smaller numbers of units, and a neural network or other machine learning model that is trained to predict interpolated pixel values using the training data. As a non-limiting example, a sample input and/or output, such as a sample picture, with sample-expanded data units (e.g., pixels added between the original pixels) may be input to a neural network or machine-learning model and output a pseudo replica sample-picture with dummy values assigned to pixels between the original pixels based on a set of interpolation rules. As a non-limiting example, in the context of an image classifier, a machine-learning model may have a set of interpolation rules trained by sets of highly detailed images and images that have been downsampled to smaller numbers of pixels, and a neural network or other machine learning model that is trained using those examples to predict interpolated pixel values in a facial picture context. As a result, an input with sample-expanded data units (the ones added between the original data units, with dummy values) may be run through a trained neural network and/or model, which may fill in values to replace the dummy values. Alternatively or additionally, processor, computing device, and/or module may utilize sample expander methods, a low-pass filter, or both. As used in this disclosure, a "low-pass filter" is a filter that passes signals with a frequency lower than a selected cutoff frequency and attenuates signals with frequencies higher than the cutoff frequency. The exact frequency response of the filter depends on the filter design. Computing device, processor, and/or module may use averaging, such as luma or chroma averaging in images, to fill in data units in between original data units.

In some embodiments, and with continued reference to FIG. 10, computing device, processor, and/or module may down-sample elements of a training example to a desired lower number of data elements. As a non-limiting example, a high pixel count image may have 256 pixels, however a desired number of pixels may be 128. Processor may down-sample the high pixel count image to convert the 256 pixels into 128 pixels. In some embodiments, processor may be configured to perform downsampling on data. Downsampling, also known as decimation, may include removing every Nth entry in a sequence of samples, all but every Nth entry, or the like, which is a process known as "compression," and may be performed, for instance by an N-sample compressor implemented using hardware or software. Anti-aliasing and/or anti-imaging filters, and/or low-pass filters, may be used to clean up side-effects of compression.

Further referring to FIG. 10, feature selection includes narrowing and/or filtering training data to exclude features and/or elements, or training data including such elements, that are not relevant to a purpose for which a trained machine-learning model and/or algorithm is being trained, and/or collection of features and/or elements, or training data including such elements, on the basis of relevance or utility for an intended task or purpose for a trained machine-learning model and/or algorithm is being trained. Feature selection may be implemented, without limitation, using any process described in this disclosure, including without limitation using training data classifiers, exclusion of outliers, or the like.

With continued reference to FIG. 10, feature scaling may include, without limitation, normalization of data entries, which may be accomplished by dividing numerical fields by norms thereof, for instance as performed for vector normalization. Feature scaling may include absolute maximum scaling, wherein each quantitative datum is divided by the maximum absolute value of all quantitative data of a set or subset of quantitative data. Feature scaling may include min-max scaling, in which each value X has a minimum value $X_{min}$ in a set or subset of values subtracted therefrom, with the result divided by the range of the values, give maximum value in the set or subset $X_{max}$:

$$X_{new} = \frac{X - X_{min}}{X_{max} - X_{min}}.$$

Feature scaling may include mean normalization, which involves use of a mean value of a set and/or subset of values, $X_{mean}$ with maximum and minimum values:

$$X_{new} = \frac{X - X_{mean}}{X_{max} - X_{min}}.$$

Feature scaling may include standardization, where a difference between X and $X_{mean}$ is divided by a standard deviation σ of a set or subset of values:

$$X_{new} = \frac{X - X_{mean}}{\sigma}.$$

Scaling may be performed using a median value of a set or subset $X_{median}$ and/or interquartile range (IQR), which represents the difference between the $25^{th}$ percentile value and the $50^{th}$ percentile value (or closest values thereto by a rounding protocol), such as:

$$X_{new} = \frac{X - X_{median}}{IQR}.$$

Persons skilled in the art, upon reviewing the entirety of this disclosure, will be aware of various alternative or additional approaches that may be used for feature scaling.

Further referring to FIG. 10, computing device, processor, and/or module may be configured to perform one or more processes of data augmentation. "Data augmentation" as used in this disclosure is addition of data to a training set using elements and/or entries already in the dataset. Data augmentation may be accomplished, without limitation, using interpolation, generation of modified copies of existing entries and/or examples, and/or one or more generative AI processes, for instance using deep neural networks and/or generative adversarial networks; generative processes may be referred to alternatively in this context as "data synthesis" and as creating "synthetic data." Augmentation may include performing one or more transformations on data, such as geometric, color space, affine, brightness, cropping, and/or contrast transformations of images.

Still referring to FIG. 10, machine-learning module 1000 may be configured to perform a lazy-learning process 1020 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 1004. Heuristic may include selecting some number of highest-ranking associations and/or training data 1004 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 10, machine-learning processes as described in this disclosure may be used to generate machine-learning models 1024. A "machine-learning model," as used in this disclosure, is a data structure representing and/or instantiating a mathematical and/or algorithmic representation of a relationship between inputs and outputs, as generated using any machine-learning process including without limitation any process as described above, and stored in memory; an input is submitted to a machine-learning model 1024 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 1024 may be generated by creating an artificial neural network, such as a convolutional neural network comprising an input layer of nodes, one or more intermediate layers, and an output layer of nodes. Connections between nodes may be created via the process of "training" the network, in which elements from a training data 1004 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 10, machine-learning algorithms may include at least a supervised machine-learning process 1028. At least a supervised machine-learning process 1028, as defined herein, include algorithms that receive a training set relating a number of inputs to a number of outputs, and seek to generate one or more data structures representing and/or instantiating one or more mathematical relations relating inputs to outputs, where each of the one or more mathematical relations is optimal according to some criterion specified to the algorithm using some scoring function. For instance, a supervised learning algorithm may include inputs such as user data, feedback data and/or adaptability data and outputs include outputs such as habituation program and/or updated habituation program as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 1004. Persons skilled in the art, upon reviewing the entirety of this disclosure, will be aware of various possible variations of at least a supervised machine-learning process 1028 that may be used to determine relation between inputs and outputs. Supervised machine-learning processes may include classification algorithms as defined above.

With further reference to FIG. 10, training a supervised machine-learning process may include, without limitation, iteratively updating coefficients, biases, weights based on an error function, expected loss, and/or risk function. For instance, an output generated by a supervised machine-learning model using an input example in a training example may be compared to an output example from the training example; an error function may be generated based on the comparison, which may include any error function suitable for use with any machine-learning algorithm described in this disclosure, including a square of a difference between one or more sets of compared values or the like. Such an error function may be used in turn to update one or more weights, biases, coefficients, or other parameters of a machine-learning model through any suitable process including without limitation gradient descent processes, least-squares processes, and/or other processes described in this disclosure. This may be done iteratively and/or recursively to gradually tune such weights, biases, coefficients, or other parameters. Updating may be performed, in neural networks, using one or more back-propagation algorithms. Iterative and/or recursive updates to weights, biases, coefficients, or other parameters as described above may be performed until currently available training data is exhausted and/or until a convergence test is passed, where a "convergence test" is a test for a condition selected as indicating that a model and/or weights, biases, coefficients, or other parameters thereof has reached a degree of accuracy. A convergence test may, for instance, compare a difference between two or more successive errors or error function values, where differences below a threshold amount may be taken to indicate convergence. Alternatively or additionally, one or more errors and/or error function values evaluated in training iterations may be compared to a threshold.

Still referring to FIG. 10, a computing device, processor, and/or module may be configured to perform method, method step, sequence of method steps and/or algorithm described in reference to this figure, in any order and with any degree of repetition. For instance, a computing device, processor, and/or module may be configured to perform a single step, sequence and/or algorithm repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. A computing device, processor, and/or module may perform any step, sequence of steps, or algorithm in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Further referring to FIG. 10, machine learning processes may include at least an unsupervised machine-learning processes 1032. An unsupervised machine-learning process, as used herein, is a process that derives inferences in datasets without regard to labels; as a result, an unsupervised machine-learning process may be free to discover any structure, relationship, and/or correlation provided in the data. Unsupervised processes 1032 may not require a response variable; unsupervised processes 1032 may be used to find interesting patterns and/or inferences between variables, to determine a degree of correlation between two or more variables, or the like.

Still referring to FIG. 10, machine-learning module 1000 may be designed and configured to create a machine-learning model 1024 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 10, machine-learning algorithms may include, without limitation, linear discriminant analysis. Machine-learning algorithm may include quadratic discriminant analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include various forms of latent space regularization such as variational regularization. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized trees, AdaBoost, gradient tree boosting, and/or voting classifier methods. Machine-learning algorithms may include neural net algorithms, including convolutional neural net processes.

Still referring to FIG. 10, a machine-learning model and/or process may be deployed or instantiated by incorporation into a program, apparatus, system and/or module. For instance, and without limitation, a machine-learning model, neural network, and/or some or all parameters thereof may be stored and/or deployed in any memory or circuitry. Parameters such as coefficients, weights, and/or biases may be stored as circuit-based constants, such as arrays of wires and/or binary inputs and/or outputs set at logic "1" and "0" voltage levels in a logic circuit to represent a number according to any suitable encoding system including twos complement or the like or may be stored in any volatile and/or non-volatile memory. Similarly, mathematical operations and input and/or output of data to or from models, neural network layers, or the like may be instantiated in hardware circuitry and/or in the form of instructions in firmware, machine-code such as binary operation code instructions, assembly language, or any higher-order programming language. Any technology for hardware and/or software instantiation of memory, instructions, data structures, and/or algorithms may be used to instantiate a machine-learning process and/or model, including without limitation any combination of production and/or configuration of non-reconfigurable hardware elements, circuits, and/or modules such as without limitation ASICs, production and/or configuration of reconfigurable hardware elements, circuits, and/or modules such as without limitation FPGAs, production and/or of non-reconfigurable and/or configuration non-rewritable memory elements, circuits, and/or modules such as without limitation non-rewritable ROM, production and/or configuration of reconfigurable and/or rewritable memory elements, circuits, and/or modules such as without limitation rewritable ROM or other memory technology described in this disclosure, and/or production and/or configuration of any computing device and/or component thereof as described in this disclosure. Such deployed and/or instantiated machine-learning model and/or algorithm may receive inputs from any other process, module, and/or component described in this disclosure, and produce outputs to any other process, module, and/or component described in this disclosure.

Continuing to refer to FIG. 10, any process of training, retraining, deployment, and/or instantiation of any machine-learning model and/or algorithm may be performed and/or repeated after an initial deployment and/or instantiation to correct, refine, and/or improve the machine-learning model and/or algorithm. Such retraining, deployment, and/or instantiation may be performed as a periodic or regular process, such as retraining, deployment, and/or instantiation at regular elapsed time periods, after some measure of volume such as a number of bytes or other measures of data processed, a number of uses or performances of processes described in this disclosure, or the like, and/or according to a software, firmware, or other update schedule. Alternatively or additionally, retraining, deployment, and/or instantiation may be event-based, and may be triggered, without limitation, by user inputs indicating sub-optimal or otherwise problematic performance and/or by automated field testing and/or auditing processes, which may compare outputs of machine-learning models and/or algorithms, and/or errors and/or error functions thereof, to any thresholds, convergence tests, or the like, and/or may compare outputs of processes described herein to similar thresholds, convergence tests or the like. Event-based retraining, deployment, and/or instantiation may alternatively or additionally be triggered by receipt and/or generation of one or more new training examples; a number of new training examples may be compared to a preconfigured threshold, where exceeding the preconfigured threshold may trigger retraining, deployment, and/or instantiation.

Still referring to FIG. 10, retraining and/or additional training may be performed using any process for training described above, using any currently or previously deployed version of a machine-learning model and/or algorithm as a starting point. Training data for retraining may be collected, preconditioned, sorted, classified, sanitized or otherwise processed according to any process described in this disclosure. Training data may include, without limitation, training examples including inputs and correlated outputs used, received, and/or generated from any version of any system, module, machine-learning model or algorithm, apparatus, and/or method described in this disclosure; such examples may be modified and/or labeled according to user feedback or other processes to indicate desired results, and/or may have actual or measured results from a process being modeled and/or predicted by system, module, machine-learning model or algorithm, apparatus, and/or method as "desired" results to be compared to outputs for training processes as described above.

Redeployment may be performed using any reconfiguring and/or rewriting of reconfigurable and/or rewritable circuit and/or memory elements; alternatively, redeployment may be performed by production of new hardware and/or software components, circuits, instructions, or the like, which may be added to and/or may replace existing hardware and/or software components, circuits, instructions, or the like.

Further referring to FIG. 10, one or more processes or algorithms described above may be performed by at least a dedicated hardware unit 1036. A "dedicated hardware unit," for the purposes of this figure, is a hardware component, circuit, or the like, aside from a principal control circuit and/or processor performing method steps as described in this disclosure, that is specifically designated or selected to perform one or more specific tasks and/or processes described in reference to this figure, such as without limitation preconditioning and/or sanitization of training data and/or training a machine-learning algorithm and/or model. A dedicated hardware unit 1036 may include, without limitation, a hardware unit that can perform iterative or massed calculations, such as matrix-based calculations to update or tune parameters, weights, coefficients, and/or biases of machine-learning models and/or neural networks, efficiently using pipelining, parallel processing, or the like; such a hardware unit may be optimized for such processes by, for instance, including dedicated circuitry for matrix and/or signal processing operations that includes, e.g., multiple arithmetic and/or logical circuit units such as multipliers and/or adders that can act simultaneously and/or in parallel or the like. Such dedicated hardware units 1036 may include, without limitation, graphical processing units (GPUs), dedicated signal processing modules, FPGA or other reconfigurable hardware that has been configured to instantiate parallel processing units for one or more specific tasks, or the like, A computing device, processor, apparatus, or module may be configured to instruct one or more dedicated hardware units 1036 to perform one or more operations described herein, such as evaluation of model and/or algorithm outputs, one-time or iterative updates to parameters, coefficients, weights, and/or biases, and/or any other operations such as vector and/or matrix operations as described in this disclosure.

Figure 11:
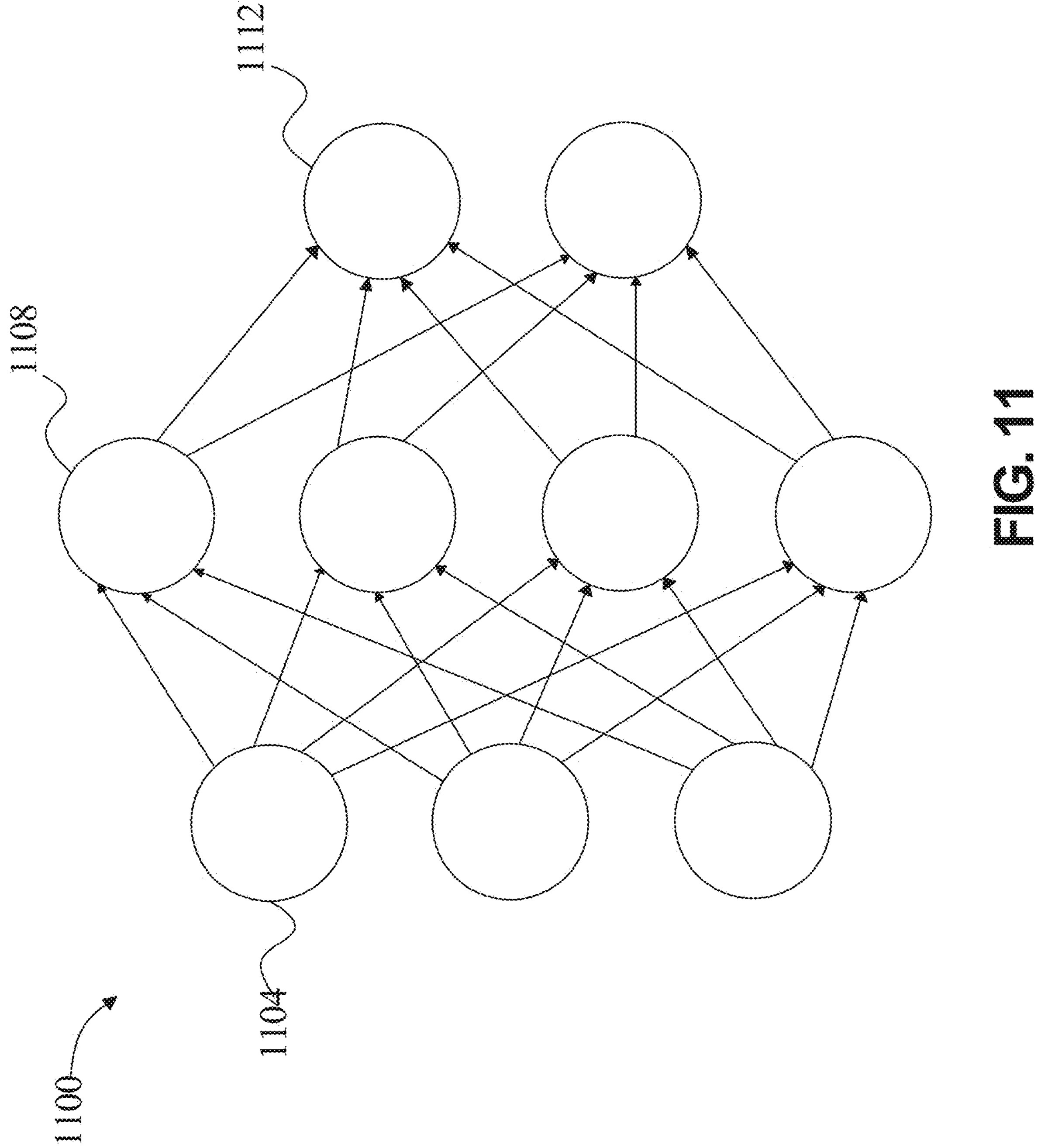
FIG. 11 is a diagram of an exemplary embodiment of a neural network.

Referring now to FIG. 11, an exemplary embodiment of neural network 1100 is illustrated. A neural network 1100 also known as an artificial neural network, is a network of "nodes," or data structures having one or more inputs, one or more outputs, and a function determining outputs based on inputs. Such nodes may be organized in a network, such as without limitation a convolutional neural network, including an input layer of nodes 1104, one or more intermediate layers 1108, and an output layer of nodes 1112. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. Connections may run solely from input nodes toward output nodes in a "feed-forward" network or may feed outputs of one layer back to inputs of the same or a different layer in a "recurrent network." As a further non-limiting example, a neural network may include a convolutional neural network comprising an input layer of nodes, one or more intermediate layers, and an output layer of nodes. A "convolutional neural network," as used in this disclosure, is a neural network in which at least one hidden layer is a convolutional layer that convolves inputs to that layer with a subset of inputs known as a "kernel," along with one or more additional layers such as pooling layers, fully connected layers, and the like.

Figure 12:
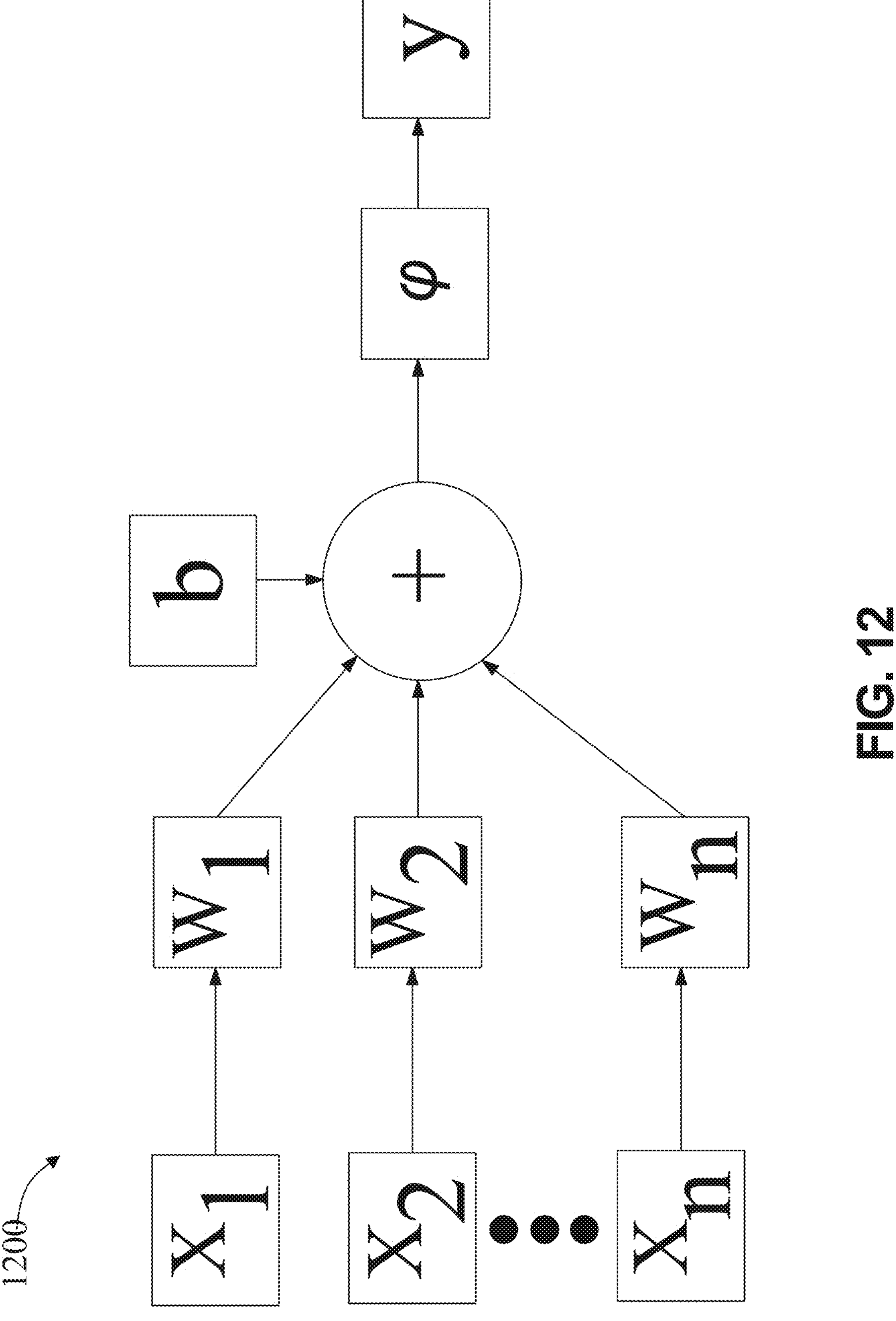
FIG. 12 is a diagram of an exemplary embodiment of a node of a neural network.

Referring now to FIG. 12, an exemplary embodiment of a node 1200 of a neural network is illustrated. A node may include, without limitation, a plurality of inputs x; that may receive numerical values from inputs to a neural network containing the node and/or from other nodes. Node may perform one or more activation functions to produce its output given one or more inputs, such as without limitation computing a binary step function comparing an input to a threshold value and outputting either a logic 1 or logic 0 output or something equivalent, a linear activation function whereby an output is directly proportional to the input, and/or a non-linear activation function, wherein the output is not proportional to the input. Non-linear activation functions may include, without limitation, a sigmoid function of the form $$f(x) = \frac{1}{1 - e^{-x}}$$

given input x, a tan h (hyperbolic tangent) function, of the form $$\frac{e^x - e^{-x}}{e^x + e^{-x}},$$

a tan h derivative function such as $f(x)=\tan h^2(x)$, a rectified linear unit function such as $f(x)=\max(0, x)$, a "leaky" and/or "parametric" rectified linear unit function such as $f(x)=\max(ax, x)$ for some a, an exponential linear units function such as $$f(x) = \begin{cases} x & \text{for } x \geq 0 \\ \alpha(e^x - 1) & \text{for } x < 0 \end{cases}$$

for some value of α (this function may be replaced and/or weighted by its own derivative in some embodiments), a softmax function such as $$f(x_i) = \frac{e^x}{\sum_i x_i}$$

where the inputs to an instant layer are $x_i$, a swish function such as $f(x)=x*\text{sigmoid}(x)$, a Gaussian error linear unit function such as $f(x)=a(1+\tanh(\sqrt{2/\pi}(x+bx^r)))$ for some values of a, b, and r, and/or a scaled exponential linear unit function such as $$f(x) = \lambda \begin{cases} \alpha(e^x - 1) & \text{for } x < 0 \\ x & \text{for } x \geq 0 \end{cases}.$$

Fundamentally, there is no limit to the nature of functions of inputs $x_i$ that may be used as activation functions. As a non-limiting and illustrative example, node may perform a weighted sum of inputs using weights $w_i$ that are multiplied by respective inputs $x_i$. Additionally or alternatively, a bias b may be added to the weighted sum of the inputs such that an offset is added to each unit in the neural network layer that is independent of the input to the layer. The weighted sum may then be input into a function φ, which may generate one or more outputs y. Weight $w_i$ applied to an input $x_i$ may indicate whether the input is "excitatory," indicating that it has strong influence on the one or more outputs y, for instance by the corresponding weight having a large numerical value, and/or a "inhibitory," indicating it has a weak effect influence on the one more inputs y, for instance by the corresponding weight having a small numerical value. The values of weights $w_i$ may be determined by training a neural network using training data, which may be performed using any suitable process as described above.

Figure 13:
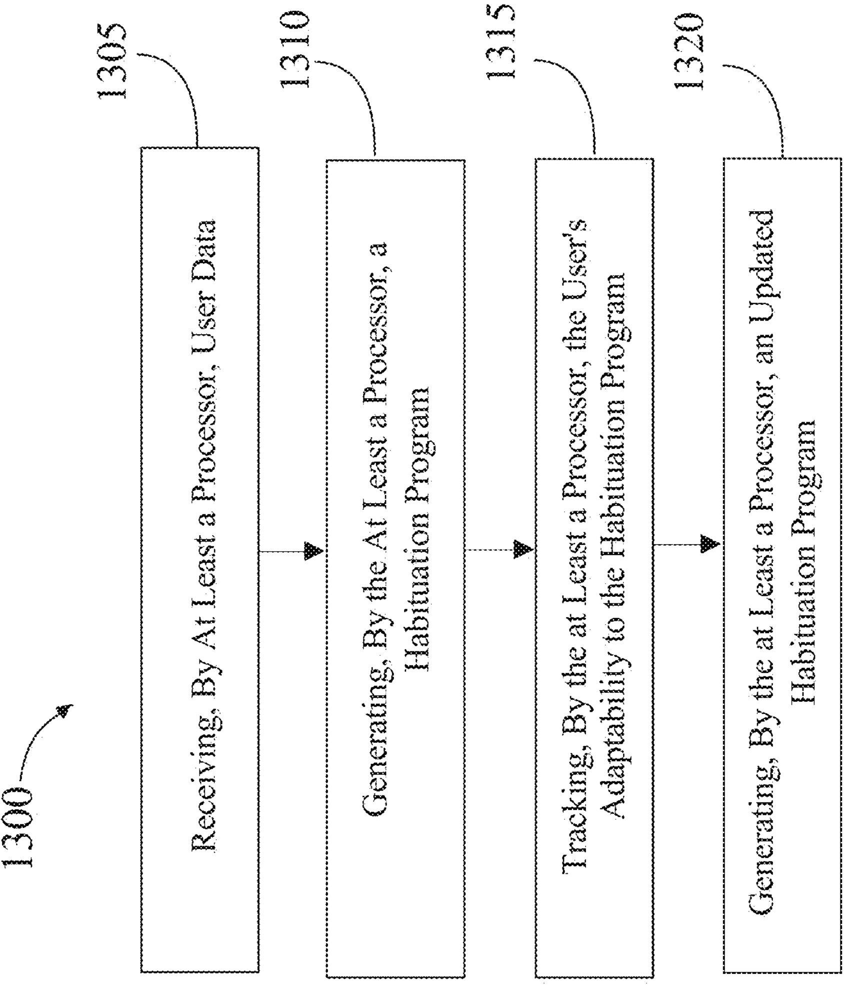
FIG. 13 is a flow diagram illustrating an exemplary embodiment of a method for tracking neurological improvements in accordance with the subject disclosure.

Referring now to FIG. 13, an exemplary method 1300 for tracking neurological improvement is described. At step 1305, method 1300 includes receiving, by at least a processor, user data from a user associated with at least a neurological behavior. This may be implemented with reference to FIGS. 1-8 and without limitation.

With continued reference to FIG. 13, at step 1310, method 1300 includes generating, by the at least a processor, a habituation program as a function of the user data and a machine learning process, wherein generating the habituation program includes iteratively training a habituation machine learning model by receiving feedback data and adjusting one or more parameter values of the habituation machine learning model as a function of the feedback data. In one or more embodiments, the one or more parameter values include a weight associated with the machine learning model. In one or more embodiments, the neurological behavior includes a habitual deficiency and generating, by the at least a processor, the habituation program as a function of the user data and the machine learning processes includes classifying the neurological behavior to a neurological class and generating the habituation program as a function of the neurological behavior and the classification. This may be implemented with reference to FIGS. 1-8 and without limitation.

With continued reference to FIG. 13, at step 1315, method 1300 includes tracking, by the at least a processor, a user's adaptability to the habituation program. In one or more embodiments, tracking, by the at least a processor, the user's adaptability to the habituation program includes receiving a current physiological response from one or more sensors in contact with the user and comparing the current physiological response to one or more previous physiological responses. In one or more embodiments, the one or more sensors include a wearable device. In one or more embodiments, receiving the current physiological response from one or more sensors in contact with the user includes receiving heart rate data from one or more the one or more sensors, receiving physiological training data comprising a plurality of heart rate data correlated to a plurality of current physiological responses, training a physiological machine learning model as a function of the physiological training data and generating the current physiological response as a function of the heart rate data and the physiological machine learning model. In one or more embodiments, the current physiological response includes a neurological impact on the user. In one or more embodiments, tracking, by the at least a processor, the user's adaptability to the habituation program includes receiving the feedback data from the user. This may be implemented with reference to FIGS. 1-8 and without limitation.

With continued reference to FIG. 13 at step 1320, method 1300 includes generating, by the at least a processor, an updated habituation program as a function of the user's adaptability to the habituation program. In one or more embodiments, the updated habituation program includes a neurological improvement of the user. In one or more embodiments, generating, by the at least a processor, the updated habituation program as a function of the user's adaptability to the habituation program further includes generating the updated habituation program as a function of the feedback data. In one or more embodiments, method 1300 further includes generating, by the at least a processor, a user interface data structure as a function of the updated habituation program and displaying, by the at least a processor, the updated habituation program through a graphical user interface as a function of the user interface data structure. This may be implemented with reference to FIGS. 1-8 and without limitation.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 14:
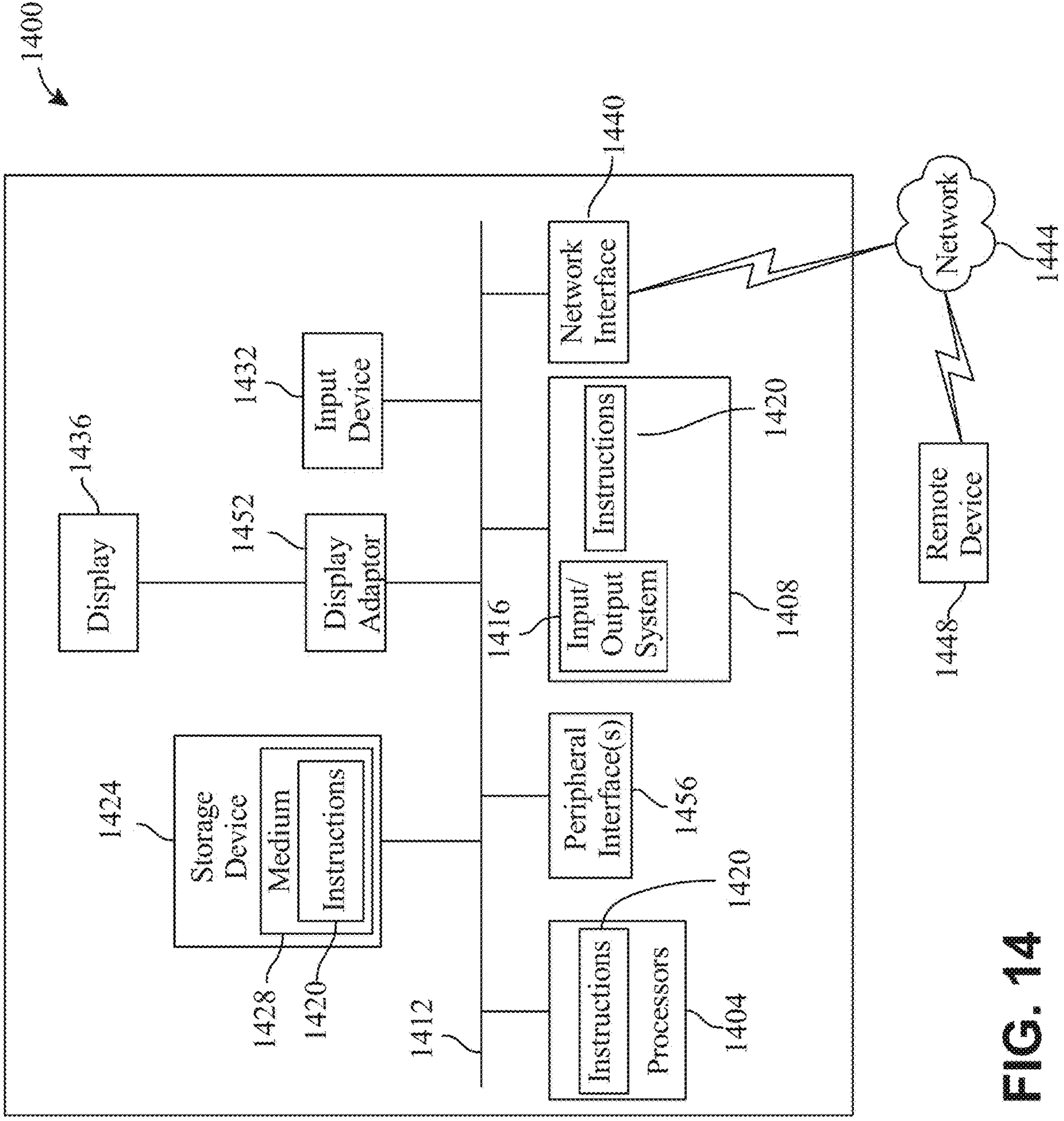
FIG. 14 is a block diagram of a computing system that can be used to implement any one or more of the methodologies disclosed herein and any one or more portions thereof. The drawings are not necessarily to scale and may be illustrated by phantom lines, diagrammatic representations and fragmentary views. In certain instances, details that are not necessary for an understanding of the embodiments or that render other details difficult to perceive may have been omitted.

FIG. 14 shows a diagrammatic representation of one embodiment of a computing device in the exemplary form of a computer system 1400 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 1400 includes a processor 1404 and a memory 1408 that communicate with each other, and with other components, via a bus 1412. Bus 1412 may include any of several types of bus structures including, but not limited to, a memory bus, a memory controller, a peripheral bus, a local bus, and any combinations thereof, using any of a variety of bus architectures.

Processor 1404 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 1404 may be organized according to Von Neumann and/or Harvard architecture as a non-limiting example. Processor 1404 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), system on module (SOM), and/or system on a chip (SoC).

Memory 1408 may include various components (e.g., machine-readable media) including, but not limited to, a random-access memory component, a read only component, and any combinations thereof. In one example, a basic input/output system 1416 (BIOS), including basic routines that help to transfer information between elements within computer system 1400, such as during start-up, may be stored in memory 1408. Memory 1408 may also include (e.g., stored on one or more machine-readable media) instructions (e.g., software) 1420 embodying any one or more of the aspects and/or methodologies of the present disclosure. In another example, memory 1408 may further include any number of program modules including, but not limited to, an operating system, one or more application programs, other program modules, program data, and any combinations thereof.

Computer system 1400 may also include a storage device 1424. Examples of a storage device (e.g., storage device 1424) include, but are not limited to, a hard disk drive, a magnetic disk drive, an optical disc drive in combination with an optical medium, a solid-state memory device, and any combinations thereof. Storage device 1424 may be connected to bus 1412 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 1424 (or one or more components thereof) may be removably interfaced with computer system 1400 (e.g., via an external port connector (not shown)). Particularly, storage device 1424 and an associated machine-readable medium 1428 may provide nonvolatile and/or volatile storage of machine-readable instructions, data structures, program modules, and/or other data for computer system 1400. In one example, software 1420 may reside, completely or partially, within machine-readable medium 1428. In another example, software 1420 may reside, completely or partially, within processor 1404.

Computer system 1400 may also include an input device 1432. In one example, a user of computer system 1400 may enter commands and/or other information into computer system 1400 via input device 1432. Examples of an input device 1432 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 1432 may be interfaced to bus 1412 via any of a variety of interfaces (not shown) including, but not limited to, a serial interface, a parallel interface, a game port, a USB interface, a FIREWIRE interface, a direct interface to bus 1412, and any combinations thereof. Input device 1432 may include a touch screen interface that may be a part of or separate from display 1436, discussed further below. Input device 1432 may be utilized as a user selection device for selecting one or more graphical representations in a graphical interface as described above.

A user may also input commands and/or other information to computer system 1400 via storage device 1424 (e.g., a removable disk drive, a flash drive, etc.) and/or network interface device 1440. A network interface device, such as network interface device 1440, may be utilized for connecting computer system 1400 to one or more of a variety of networks, such as network 1444, and one or more remote devices 1448 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 1444, may employ a wired and/or a wireless mode of communication. In general, any network topology may be used. Information (e.g., data, software 1420, etc.) may be communicated to and/or from computer system 1400 via network interface device 1440.

Computer system 1400 may further include a video display adapter 1452 for communicating a displayable image to a display device, such as display 1436. Examples of a display device include, but are not limited to, a liquid crystal display (LCD), a cathode ray tube (CRT), a plasma display, a light emitting diode (LED) display, and any combinations thereof. Display adapter 1452 and display 1436 may be utilized in combination with processor 1404 to provide graphical representations of aspects of the present disclosure. In addition to a display device, computer system 1400 may include one or more other peripheral output devices including, but not limited to, an audio speaker, a printer, and any combinations thereof. Such peripheral output devices may be connected to bus 1412 via a peripheral interface 1456. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A system for tracking user data, the system comprising:

a processor; and a memory communicatively connected to the processor, the memory containing instructions configuring the processor to:

receive user data pertaining to a user, wherein the user data comprises physiological response data associated with at least a neurological behavior, wherein the user data is received using:

a sense board comprising a circuit board including a plurality of sensors configured to detect sensor inputs; and generate a habituation program as a function of the user data and a machine learning process, wherein generating the habituation program comprises:

iteratively training a habituation machine learning model by receiving feedback data and adjusting one or more parameter values of the habituation machine learning model as a function of the feedback data;

wherein the habituation machine learning model comprises a transformer architecture operable to process sequential input data and configured to be used with an attention mechanism and positional encoding, wherein the attention mechanism is operable to enable quantification of features of the input data, wherein the attention mechanism utilizes at least one multi-head self-attention mechanism to dynamically weight the physiological response data as a function of at least a correlation between the physiological response data and feedback data, and wherein the positional encoding is operable to encode a position of an entity in a sequence;

track a user's adaptability to the habituation program, wherein tracking the user's adaptability to the habituation program comprises receiving adaptability data comprising at least a physiological response data of the user, wherein the at least a physiological response data is collected after deploying the habituation program; and generate an updated habituation program as a function of the user's adaptability to the habituation program, wherein the updated habituation program comprises modified treatment instructions, and wherein the modified treatment instructions comprise:

replacing steps associated with a negative physiological response; and retaining steps associated with a positive physiological response.

2. The system of claim 1, wherein tracking the user's adaptability to the habituation program comprises:

receiving a current physiological response from one or more sensors in contact with the user; and comparing the current physiological response to one or more previous physiological responses.

3. The system of claim 2, wherein the one or more sensors comprises a wearable device.

4. The system of claim 2, wherein receiving the current physiological response from the one or more sensors in contact with the user comprises:

receiving heart rate data from the one or more sensors;

receiving physiological training data comprising a plurality of heart rate data correlated to a plurality of current physiological responses;

training a physiological machine learning model as a function of the physiological training data; and generating the current physiological response as a function of the heart rate data and the physiological machine learning model.

5. The system of claim 2, wherein the current physiological response comprises a neurological impact on the user.

6. The system of claim 1, wherein:

tracking the user's adaptability to the habituation program comprises receiving the feedback data from the user.

7. The system of claim 1, wherein adjusting the one or more parameter values of the habituation machine learning model as a function of the feedback data comprises adjusting the one or more parameter values to minimize a loss function.

8. The system of claim 1, wherein the processor is further configured to:

generate a user interface data structure as a function of the updated habituation program; and display the updated habituation program through a graphical user interface as a function of the user interface data structure.

9. The system of claim 1, wherein:

the at least a neurological behavior comprises a habitual deficiency; and generating the habituation program as a function of the user data and the machine learning process comprises:

classifying the at least a neurological behavior to at least a neurological class; and generating the habituation program as a function of the habitual deficiency and the at least a neurological class.

10. A method for tracking user data, the method comprising:

receiving, by at least a processor, user data pertaining to a user, wherein the user data comprises physiological response data associated with at least a neurological behavior, wherein the user data is received using:

a sense board comprising a circuit board including a plurality of sensors configured to detect sensor inputs; and generating, by the at least a processor, a habituation program as a function of the user data and a machine learning process, wherein generating the habituation program comprises:

iteratively training a habituation machine learning model by receiving feedback data and adjusting one or more parameter values of the habituation machine learning model as a function of the feedback data;

wherein the habituation machine learning model comprises a transformer architecture for processing sequential input data and for using an attention mechanism and positional encoding, quantifying, by the attention mechanism, features of the input data, wherein the attention mechanism utilizes at least one multi-head self-attention mechanism to dynamically weight the physiological response data as a function of at least a correlation between the physiological response data and feedback data, and encoding, by the positional encoding, a position of an entity in a sequence;

tracking, by the at least a processor, a user's adaptability to the habituation program, wherein tracking the user's adaptability to the habituation program comprises receiving adaptability data comprising at least physiological response data of the user, wherein the at least physiological response data is collected after deploying the habituation program; and generating, by the at least a processor, an updated habituation program as a function of the user's adaptability to the habituation program, wherein the updated habituation program comprises modified treatment instructions, and wherein the modified treatment instructions comprise:

replacing steps associated with a negative physiological response; and retaining steps associated with a positive physiological response.

11. The method of claim 10, wherein tracking, by the at least a processor, the user's adaptability to the habituation program comprises:

receiving a current physiological response from one or more sensors in contact with the user; and comparing the current physiological response to one or more previous physiological responses.

12. The method of claim 11, wherein the one or more sensors comprise a wearable device.

13. The method of claim 11, wherein receiving the current physiological response from the one or more sensors in contact with the user comprises:

receiving heart rate data from the one or more sensors;

receiving physiological training data comprising a plurality of heart rate data correlated to a plurality of current physiological responses;

training a physiological machine learning model as a function of the physiological training data; and generating the current physiological response as a function of the heart rate data and the physiological machine learning model.

14. The method of claim 11, wherein the current physiological response comprises a neurological impact on the user.

15. The method of claim 10, wherein:

tracking, by the at least a processor, the user's adaptability to the habituation program comprises receiving the feedback data from the user.

16. The method of claim 10, wherein adjusting the one or more parameter values of the habituation machine learning model as a function of the feedback data comprises adjusting the one or more parameter values to minimize a loss function.

17. The method of claim 10, the method further comprising:

generating, by the at least a processor, a user interface data structure as a function of the updated habituation program; and displaying, by the at least a processor, the updated habituation program through a graphical user interface as a function of the user interface data structure.

18. The method of claim 10, wherein:

the at least a neurological behavior comprises a habitual deficiency; and generating, by the at least a processor, the habituation program as a function of the user data and the machine learning process comprises:

classifying the at least a neurological behavior to at least a neurological class; and generating the habituation program as a function of the habitual deficiency and the at least a neurological class.

19. The system of claim 1, wherein the transformer architecture further comprises an encoder and a decoder configured to operate with at least one of: a multi-headed attention layer; a pointwise feed-forward layer; one or more residual connections, and layer normalization.

20. The method of claim 10, wherein the transformer architecture further comprises an encoder and a decoder configured to operate with at least one of: a multi-headed attention layer; a pointwise feed-forward layer; one or more residual connections, and layer normalization.

* * * * *